US006346615B1

(12) United States Patent
Bronstein et al.

(10) Patent No.: US 6,346,615 B1
(45) Date of Patent: *Feb. 12, 2002

(54) CHEMILUMINESCENT 1,2-DIOXETANES

(75) Inventors: Irena Bronstein, Newton; Brooks Edwards, Cambridge; Alison Sparks, North Andover, all of MA (US)

(73) Assignee: Tropix, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/656,213

(22) Filed: Sep. 6, 2000

Related U.S. Application Data

(60) Continuation of application No. 09/296,539, filed on Apr. 22, 1999, now Pat. No. 6,140,495, which is a continuation of application No. 08/904,847, filed on Aug. 1, 1997, now Pat. No. 6,022,964, which is a continuation of application No. 08/588,810, filed on Jan. 19, 1996, now Pat. No. 5,851,771, which is a continuation of application No. 08/057,903, filed on May 7, 1993, now Pat. No. 5,538,847, which is a continuation-in-part of application No. 07/806,928, filed on Dec. 12, 1991, now Pat. No. 5,330,900, which is a division of application No. 07/574,786, filed on Aug. 30, 1990, now Pat. No. 5,112,960, which is a continuation-in-part of application No. 07/559,152, filed on Jul. 25, 1990, now abandoned, which is a division of application No. 07/367,772, filed on Jul. 17, 1989, now abandoned, which is a division of application No. 07/140,197, filed on Dec. 31, 1997, now abandoned.

(51) Int. Cl.[7] ................ C07H 19/04; C07D 327/06; C07F 9/06; C07F 9/28; C07F 9/02

(52) U.S. Cl. ............... 536/26.6; 549/16; 549/218; 549/220; 252/700; 558/194

(58) Field of Search ................... 549/16; 435/6

(56) References Cited

U.S. PATENT DOCUMENTS

| | | |
|---|---|---|
| 4,931,223 A | 6/1990 | Bronstein et al. |
| 4,952,707 A | 8/1990 | Edwards et al. |
| 4,956,477 A | 9/1990 | Bronstein et al. |
| 4,959,182 A | 9/1990 | Schaap |
| 4,962,192 A | 10/1990 | Schaap |
| 4,978,614 A | 12/1990 | Bronstien et al. |
| 4,983,779 A | 1/1991 | Schaap |
| 5,004,565 A | 4/1991 | Schaap |
| 5,032,381 A | 7/1991 | Bronstein et al. |
| 5,089,630 A | 2/1992 | Bronstien et al. |
| 5,112,960 A | 5/1992 | Bronstein et al. |
| 5,145,772 A | 9/1992 | Voyta et al. |
| 5,177,241 A | 1/1993 | Bronstein et al. |
| 5,220,005 A | 6/1993 | Bronstein |
| 5,326,882 A | * 7/1994 | Bronstein ................... 549/16 |
| 5,330,900 A | 7/1994 | Bronstein et al. |
| 5,336,596 A | 8/1994 | Bronstein et al. |
| 5,386,017 A | 1/1995 | Schaap |
| 5,538,847 A | 7/1996 | Bronstein et al. |
| 5,543,295 A | 8/1996 | Bronstein et al. |
| 5,547,836 A | 8/1996 | Bronstein et al. |
| 5,582,980 A | 12/1996 | Bronstein et al. |
| 5,591,591 A | 1/1997 | Bronstein et al. |
| 5,593,828 A | 1/1997 | Bronstein et al. |
| 5,605,795 A | 2/1997 | Bronstein |
| 5,625,077 A | 4/1997 | Bronstein |
| 5,637,747 A | 6/1997 | Bronstein et al. |
| 5,639,907 A | 6/1997 | Bronstein et al. |
| 5,648,555 A | 7/1997 | Bronstein et al. |
| 5,652,345 A | 7/1997 | Schaap et al. |
| 5,654,154 A | 8/1997 | Bronstein et al. |
| 5,679,802 A | 10/1997 | Bronstein et al. |
| 5,679,803 A | 10/1997 | Bronstein et al. |
| 5,707,559 A | 1/1998 | Schaap et al. |
| 5,753,436 A | 5/1998 | Bronstein et al. |
| 5,756,770 A | 5/1998 | Bronstein et al. |
| 5,773,628 A | 6/1998 | Akhavan-Tafti et al. |
| 5,777,133 A | 7/1998 | Bronstein et al. |
| 5,783,381 A | 7/1998 | Bronstein et al. |
| 5,831,102 A | 11/1998 | Bronstein et al. |
| 5,840,919 A | 11/1998 | Bronstein et al. |
| 5,847,161 A | 12/1998 | Bronstein et al. |
| 5,851,771 A | 12/1998 | Bronstein et al. |
| 5,856,522 A | 1/1999 | Bronstein et al. |
| 5,866,389 A | 2/1999 | Bronstein |
| 5,869,699 A | 2/1999 | Bronstein et al. |
| 5,869,705 A | 2/1999 | Bronstein |
| 5,891,626 A | 4/1999 | Schaap |
| 5,981,768 A | 11/1999 | Bronstein et al. |
| RE36,536 E | 1/2000 | Bronstein |
| 6,022,964 A | 2/2000 | Bronstein et al. |
| 6,107,024 A | 8/2000 | Schaap |
| 6,113,816 A | 9/2000 | Bronstein |
| 6,124,478 A | 9/2000 | Bronstein et al. |
| 6,132,956 A | 10/2000 | Bronstein et al. |
| 6,133,459 A | 10/2000 | Schaap et al. |
| 6,140,495 A | 10/2000 | Bronstein et al. |

FOREIGN PATENT DOCUMENTS

| | | |
|---|---|---|
| WO | 89/06226 | 7/1989 |
| WO | 92/04341 | 3/1992 |
| WO | 92/044341 | * 3/1992 |

OTHER PUBLICATIONS

Edwards, B., Sparks, A., Voyta, J.C., Strong, R., Murphy, O., Bronstein, I., "Naphthyl Dioxetane Phosphates: Synthesis of Novel Substrates for Enzymatic Chemiluminescent Assays", J. Org. Chem. 55(25):6225–6229 (1990).

Hann & Spencer, "The Preparation of Chlorovanillin and Some of Its Derivatives", J. Am. Chem. Soc., 49:535–537 (1927).

* cited by examiner

Primary Examiner—W. Gary Jones
Assistant Examiner—Arun Kr. Chakrabarti
(74) Attorney, Agent, or Firm—Piper Marbury Rudnick & Wolfe, LLP; Steven B. Kelber

(57) ABSTRACT

Spiroadamantyl dioxetanes bearing an alkoxy substituent, and an aromatic substituent of phenyl or naphthyl on the dioxetane ring can be activated to chemiluminesce if the aromatic substituent bears a moiety designated OX, wherein the X is cleaved by an enzyme with which the dioxetane is permitted to come in contact with. The $T_{1/2}$ kinetics of the chemiluminescent reaction, as well as the signal intensity, or quantum yield of the chemiluminescent reaction, can be altered by selection of an electron-withdrawing or an electron-donating group Z, at positions on the aromatic substituent other than those adjacent the point of attachment to the dioxetane. Signal strength can further be enhanced by recognized chemiluminescent enhancers.

2 Claims, 12 Drawing Sheets

140-17

128-87

CSPD
128-87
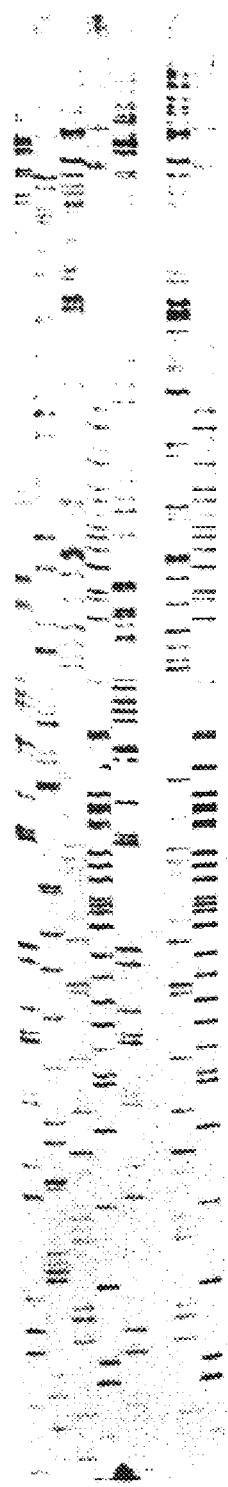
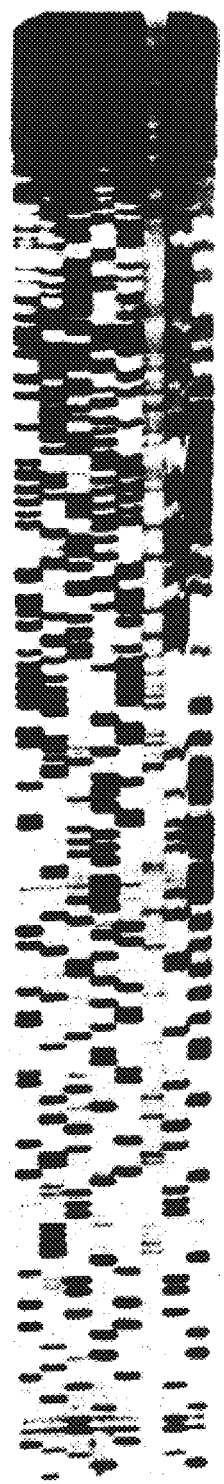
FIG.2A
FIG.2B

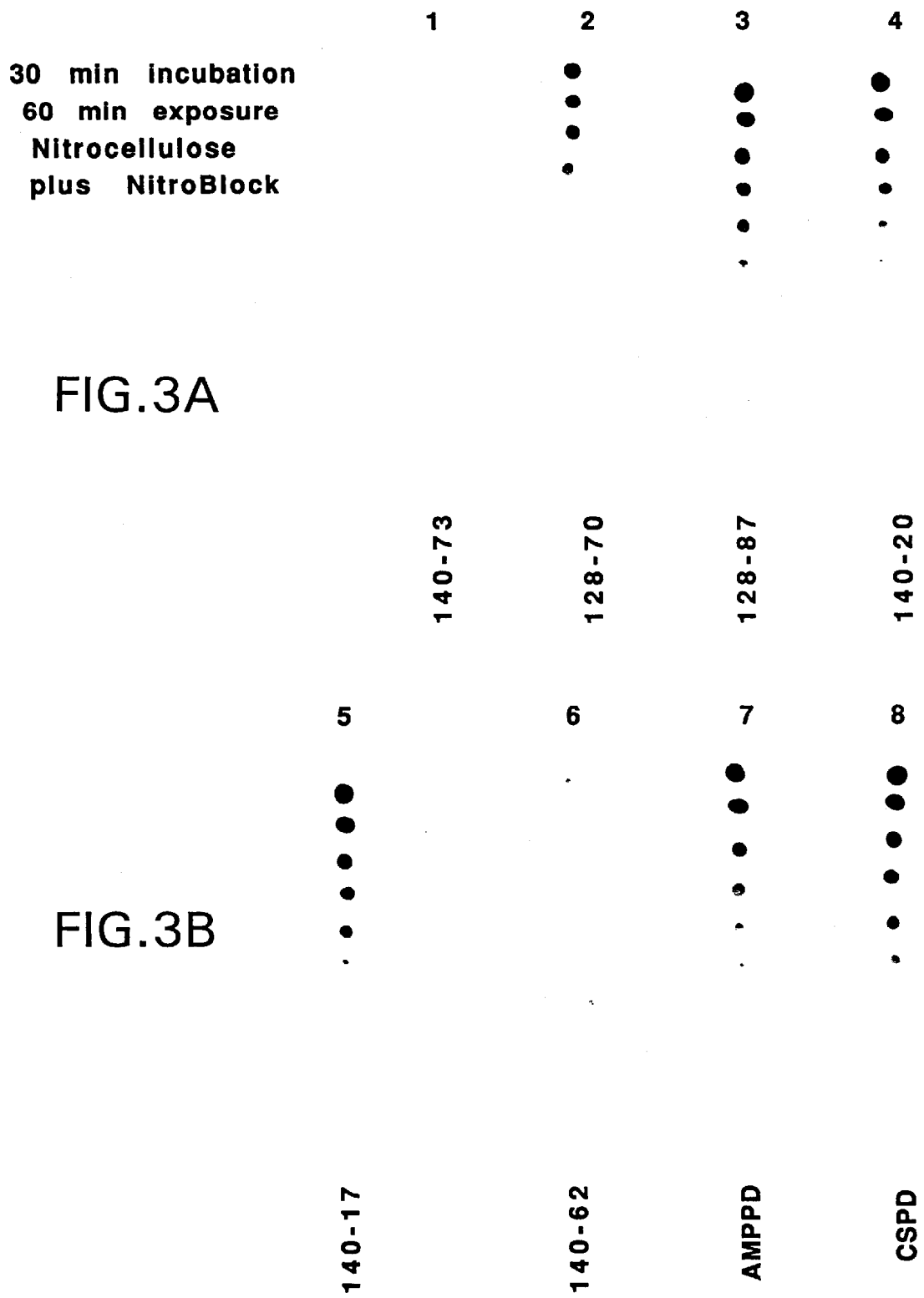

140-17  128-87  AMPPD  CSPD

NYLON
30 minute exposure
0 minute incubation 140-17  128-87  AMPPD  CSPD

NYLON
60 minute exposure
30 minute incubation 140-17     128-87     AMPPD

NITROCELLULOSE
30 minute exposure
0 minute incubation 140-17     128-87     AMPPD NITROCELLULOSE
60 minute exposure
30 minute incubation 140-17    128-87    AMPPD NITROCELLULOSE
120 minute exposure
60 minute incubation 140-17    128-87    AMPPD NITROCELLULOSE
15.5 hour exposure
2 hour incubation

| CSPD | CSPD | CSPD |
| --- | --- | --- |
| Calfax DB45 | Calfax 10L-45 | Calsoft T-60 |
| 30 min incubation | 30 min incubation | 30 min incubation |
| 60 min exposure | 60 min exposure | 60 min exposure |

| 140-17 | 140-17 | 140-17 |
| --- | --- | --- |
| Calfax DB45 | Calfax 10L-45 | Calsoft T-60 |
| 30 min incubation | 30 min incubation | 30 min incubation |
| 60 min exposure | 60 min exposure | 60 min exposure |

CSPD
Calfax DB45
30 min incubation
60 min exposure

CSPD
Calfax 10L-45
30 min incubation
60 min exposure

CSPD
Calsoft T-60
30 min incubation
60 min exposure

FIG. 10A 128-87
Calfax DB45
30 min incubation
60 min exposure 128-87
Calfax 10L-45
30 min incubation
60 min exposure 128-87
Calsoft T-60
30 min incubation
60 min exposure

FIG. 10D  FIG. 10B  FIG. 10C

CSPD
Calfax DB45
2 hr incubation
15.5 hr exposure

CSPD
Calfax 10L-45
2 hr incubation
15.5 hr exposure

CSPD
Calsoft T-60
2 hr incubation
15.5 hr exposure

FIG.11A 140-17
Calfax DB45
3 hr incubation
15 hr exposure 140-17
Calfax 10L-45
3 hr incubation
15 hr exposure 140-17
Calsoft T-60
3 hr incubation
15 hr exposure

FIG.11B

| CSPD | CSPD | CSPD |
| --- | --- | --- |
| Calfax DB45 | Calfax 10L-45 | Calsoft T-60 |
| 2 hr incubation | 2 hr incubation | 2 hr incubation |
| 15.5 hr exposure | 15.5 hr exposure | 15.5 hr exposure |

| 128-87 | 128-87 | 128-87 |
| --- | --- | --- |
| Calfax DB45 | Calfax 10L-45 | Calsoft T-60 |
| 3 hr incubation | 3 hr incubation | 3 hr incubation |
| 15 hr exposure | 15 hr exposure | 15 hr exposure |

CHEMILUMINESCENT 1,2-DIOXETANES

This application is a continuation of Ser. No. 09/296,539, Apr. 22, 1999, U.S. Pat. No. 6,140,495, which is a continuation of Ser. No. 08/904,847, Aug. 1, 1997, U.S. Pat. No. 6,022,964, which is a continuation of Ser. No. 08/588,810, Jan. 19, 1996, U.S. Pat. No. 5,851,771, which is a continuation of Ser. No. 08/057,903, May 7, 1993, U.S. Pat. No. 5,538,847, which is a continuation-in-part of Ser. No. 07/806,928, Dec. 12, 1991, U.S. Pat. No. 5,330,900, which is a division of Ser. No. 07/574,786, Aug. 30, 1990, U.S. Pat. No. 5,112,960, which is a continuation-in-part of Ser. No. 07/559,152, Jul. 25, 1990, abandoned, which is a division of Ser. No. 07/367,772, Jul. 17, 1989, abandoned, and a division of Ser. No. 07/140,197, Dec. 31, 1987, abandoned.

BACKGROUND OF THE INVENTION

1. Field of the Invention

This invention pertains to chemiluminescent 1,2-dioxetane derivatives which can be enzymatically activated to decompose and, through decomposition, release light. The dioxetanes are particularly characterized by the presence of an aromatic (phenyl or naphthyl) ring bonded to the dioxetane, which ring bears a meta-substituted or disjoint enzymatically cleavable group, which when cleaved, leaves the phenoxyanion or naphthyloxyanion of the dioxetane, and, at the four or preferably the five position, an electron donating or electron withdrawing group. By selecting the identity of the substituent at the four or five position (the Z moiety) particular aspects of the chemiluminescent properties of the dioxetane, including half life, quantum yield, S/N ratio, etc., can be altered.

2. Background of the Invention 1,2-dioxetane enzyme substrates have been well established as highly efficient chemiluminescent reporter molecules for use in enzyme immunoassays of a wide variety of types. These assays provide a preferred alternative to conventional assays that rely on radioisotopes, fluorophores, complicated color shifting, secondary reactions and the like. Dioxetanes developed for this purpose include those disclosed in U.S. Pat. No. 4,978,614 as well as U.S. Pat. No. 5,112,960. U.S. Pat. No. 4,978,614 discloses, among others, 3-(2'-spiroadamantane)4-methoxy-4-(3"-phosphoryloxy) phenyl-1,2-dioxetane, which has received world-wide attention, and is commercially available under the trade name AMPPD. U.S. Pat. No. 5,112,960, discloses similar compounds, wherein the adamantyl stabilizing ring is substituted, at either bridgehead position, with a variety of substituents, including hydroxy, halogen, and the like, which convert the otherwise static or passive adamantyl stabilizing group into an active group involved in the kinetics of decomposition of the dioxetane ring. Compounds of this type have similarly received international attention, giving a faster and stronger signal than AMPPD in many applications. CSPD corresponds to AMPPD with a chlorine substituent on the adamantyl group, and, like AMPPD, is available from Tropix, Inc. of Bedford, Mass.

Compounds of this type have been particularly developed for enhanced sensitivity in assays for the presence of analytes in concentrations as low as $10^{-12}$ M and lower. In certain applications, compounds of this type are used in conjunction with enhancers to detect analytes in concentrations of $10^{-12}$ M or lower. These enhancement agents, which include natural and synthetic water-soluble macromolecules, are disclosed in detail in U.S. Pat. No. 5,145,772. Preferred enhancement agents include water-soluble polymeric quaternary ammonium salts, such as poly (vinylbenzyltrimethylammonium chloride) (TMQ), poly (vinylbenzyltributylammonium chloride) (TBQ) and poly (vinylbenzyldimethylbenzylammonium chloride) (BDMQ).

These enhancement agents improve the chemiluminescent signal of the dioxetane reporter molecules, apparently by providing a hydrophobic environment in which the dioxetane is sequestered. Water, an unavoidable aspect of most assays, due to the use of body fluids, is a natural "quencher" of the dioxetane chemiluminescence. The enhancement molecules apparently exclude water from the microenvironment in which the dioxetane molecules, or at least the excited state emitter species reside, resulting in enhanced chemiluminescence. Other effects associated with the enhancer-dioxetane interaction could also contribute to the chemiluminescence enhancement.

Additional advantages can be secured by the use of selected membranes, including nylon membranes and treated nitrocellulose, providing a similarly hydrophobic surface for membrane-based assays, and other membranes coated with the enhancer-type polymers described.

Nonetheless, it remains a general goal of the industry to improve the performance of these stabilized, chemiluminescent dioxetane reporter molecules, to improve the machine readability, sensitivity, and performance aspects of the immunoassays, dependent on the chemiluminescent signal released by the dioxetanes.

By way of background, and as disclosed in all the patents referenced above, the enzymatically-activated dioxetanes are used as reporter molecules, as substrates for enzymes which cleave the enzyme-labile group bonded to an aromatic substituent on the dioxetane ring. Thus, the enzyme, e.g., alkaline phosphatase, is covalently linked or otherwise complexed with either an antigen or antibody, in conventional antigen/antibody ligand binding assays, or a nucleic acid probe in nucleic acid assays. The enzyme-bearing antigen or antibody, or nucleic acid probe, is then admixed with the analyte suspected of containing the target antigen, or nucleic acid sequence, under conditions which permit complexing or hybridization between the antigen/antibody or probe/nucleic acid sequence. After washing away or separating off all noncomplexed or nonhybridized material, the dioxetane substrate is added. If the suspected analyte is present, the enzyme will cleave the enzyme-labile group on the aromatic substituent on the dioxetane, e.g., phenyl or naphthyl, yielding the phenoxy or naphthyloxy anion intermediate. This anion decomposes, by electron transfer through the aromatic ring, cleaving the dioxetane ring, and yielding two carbonyl-based products. The cleavage/decomposition event is the light-releasing event.

To automate clinical assays, and to provide for substantial throughput, continued reductions in the halflife, or $T_{1/2}$ of the dioxetane, as well as a reduction in the amount of time required to reach the maximum emission of light of the reporter molecule, is desirable. At the same time, to detect analytes in extremely low concentrations, below, e.g., about $10^{-12}$ M, it is desirable to improve the intensity of the signal of the dioxetane reporter molecule, and simultaneously desirable to avoid increasing the background noise due to nonenzymatically-induced light release, so as to improve the overall sensitivity of the assay. Thus, further improvements in chemiluminescent dioxetane reporter molecules are sought.

SUMMARY OF THE INVENTION

The above goals, and others, are met by a new class of dioxetanes, particularly characterized by a substituent on the aromatic ring bonded to the dioxetane, in addition to the meta-substituted enzyme-labile group. Thus, the novel dioxetanes of this invention have the generalized structure I, II or III below.

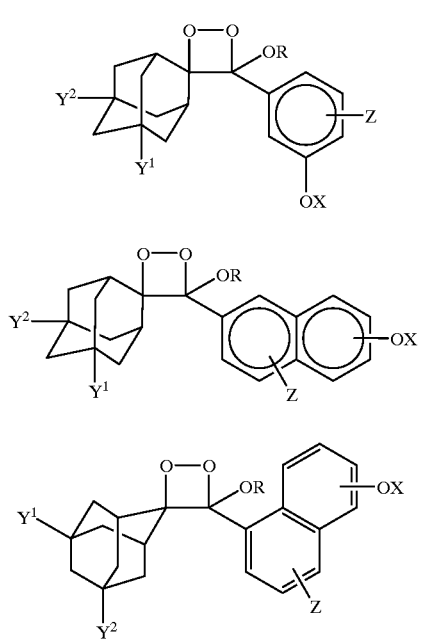

wherein R is C1–12 alkyl, aralkyl, or aryl, preferably C1–6 alkyl, X is an enzyme labile group cleavable by a specific enzyme which recognizes that group to leave the phenoxy or naphthoxy anion, and is preferably a phosphate or galactoside, $Y^1$ and $Y^2$ are independently hydrogen, or an electron donating or withdrawing group, and are preferably hydrogen, methoxy, carboxy, or halogen, and most preferably one of $Y^1$ and $Y^2$ is hydrogen while the other is chlorine, and Z is an electron-active group, most preferably chlorine, alkoxy, alkyl or amido. When Z is on a phenyl ring, Z is in the four or five position, preferably the five position. When OX and Z are substituted on a naphthyl group, OX is substituted such that the substitution is disjoint, that is the total number of ring atoms between the point of attachment to the dioxetane ring and the point of substitution, including the point of attachment and substitution, is an odd number, as disclosed in U.S. Pat. No. 4,952,707. Substituent Z may be substituted on the naphthyl ring at any position other than those adjacent the one position, or the point of attachment to the dioxetane ring.

By selecting the particular identity of Z, as an electron-withdrawing or an electron-donating group, specific characteristics of the chemiluminescent behavior of the dioxetane, including its $T_{1/2}$, time to maximum emission, maximum emission wavelength, and chemiluminescent signal intensity can be affected.

BRIEF DESCRIPTION OF THE DRAWINGS

FIGS. 1 and 2 are electrophotographic duplications of x-ray film images of DNA sequencing obtained by use of the dioxetanes of the claimed invention. These are compared against the current commercial standard, CSPD.

FIGS. 3–12 are electrophotographic duplications of dot blot assay results on membranes as indicated, employing dioxetanes of the claimed invention, dioxetanes outside the scope of the claimed invention and the commercial standards CSPD and AMPPD. The membrane on which these assays were conducted is set forth in the figures.

DETAILED DESCRIPTION OF THE INVENTION

Figure 1A:
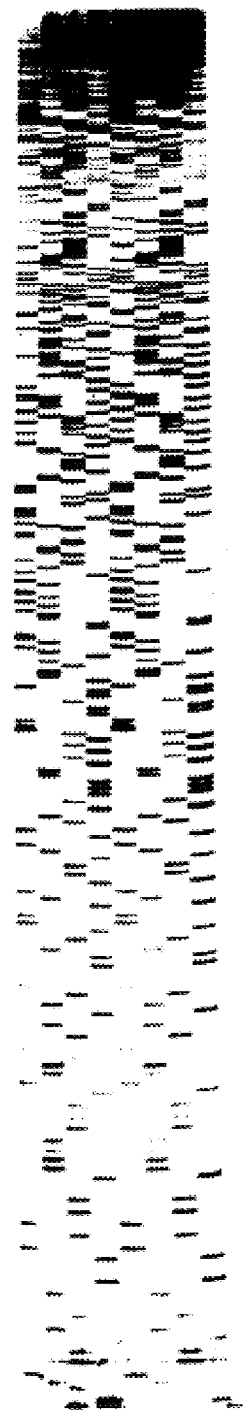
Figure 1B:
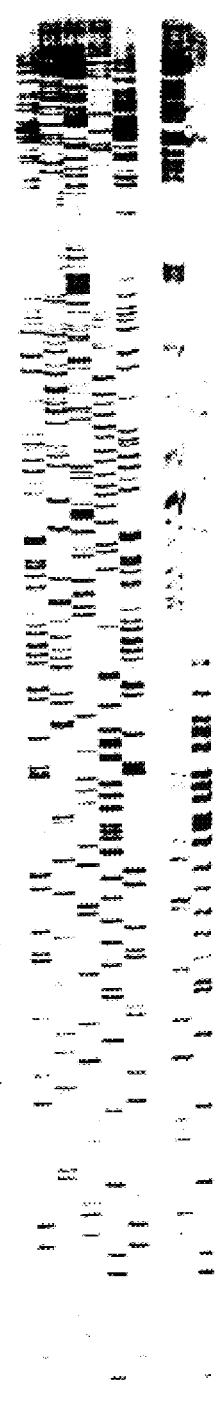
Figure 4:
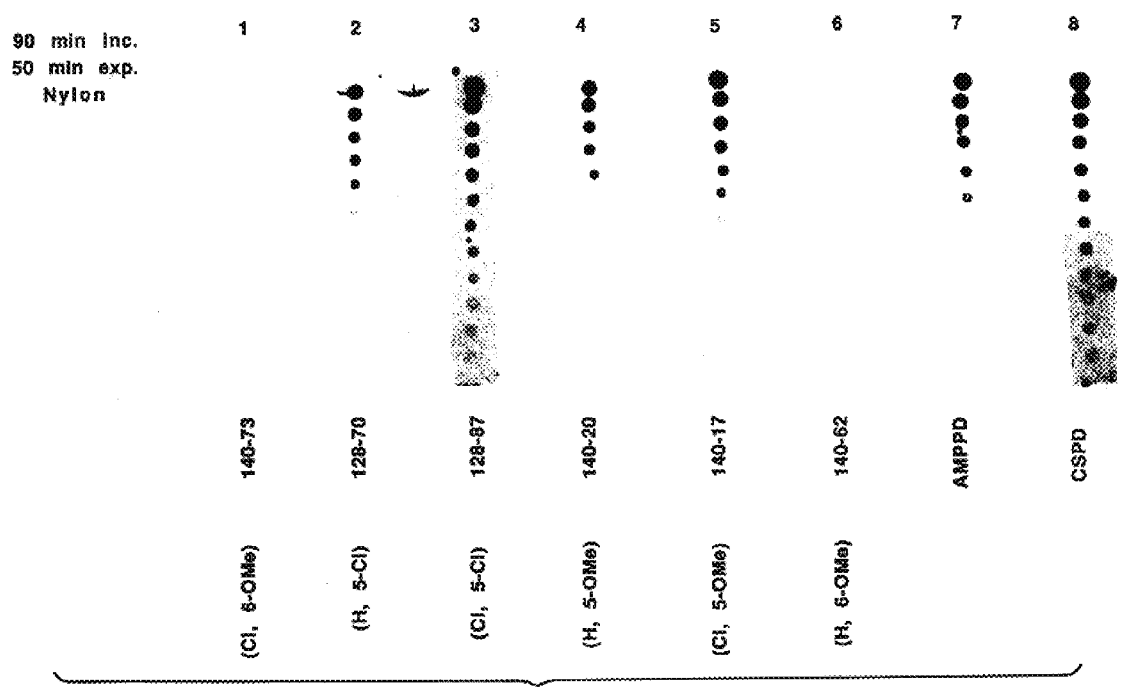
Figures 5A, 5B:
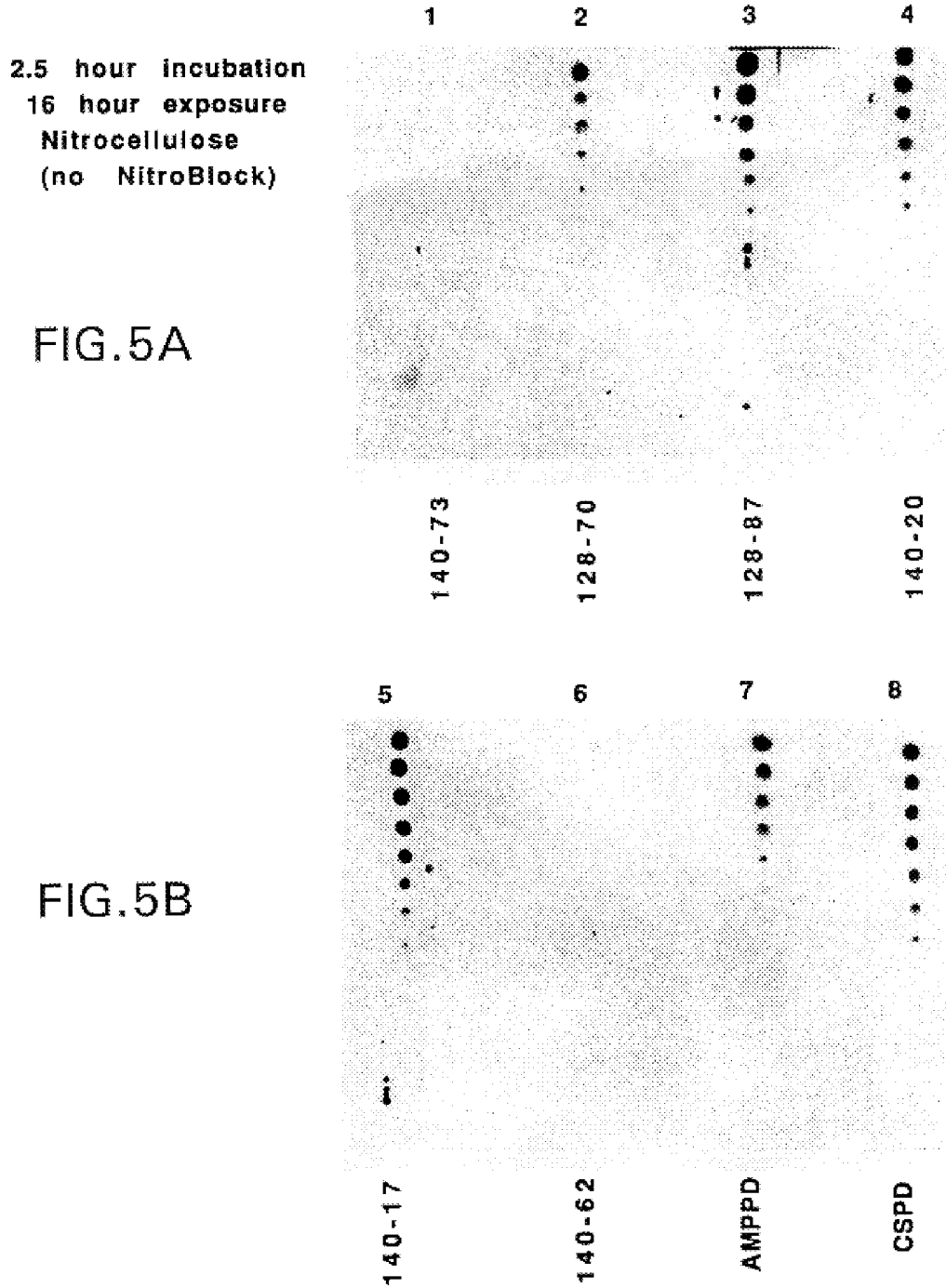
Figure 6A:
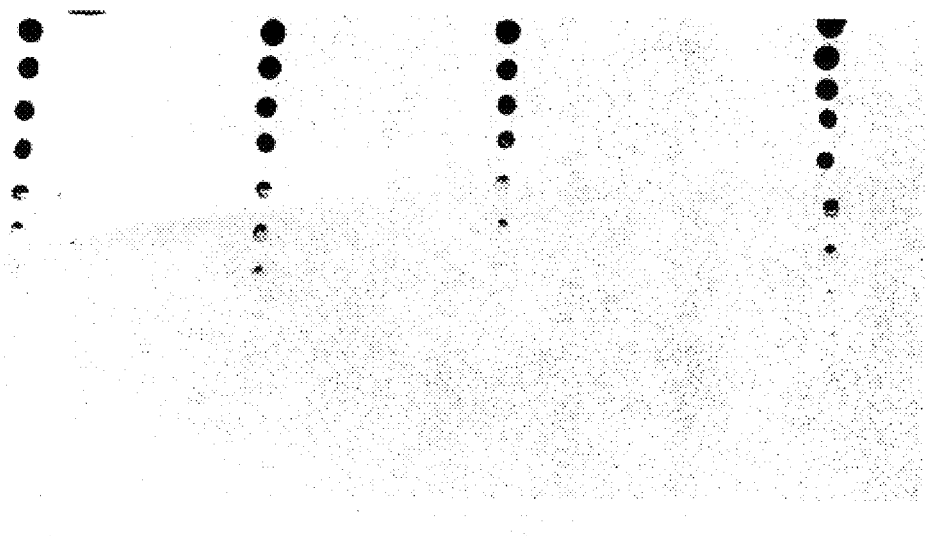
Figure 6B:
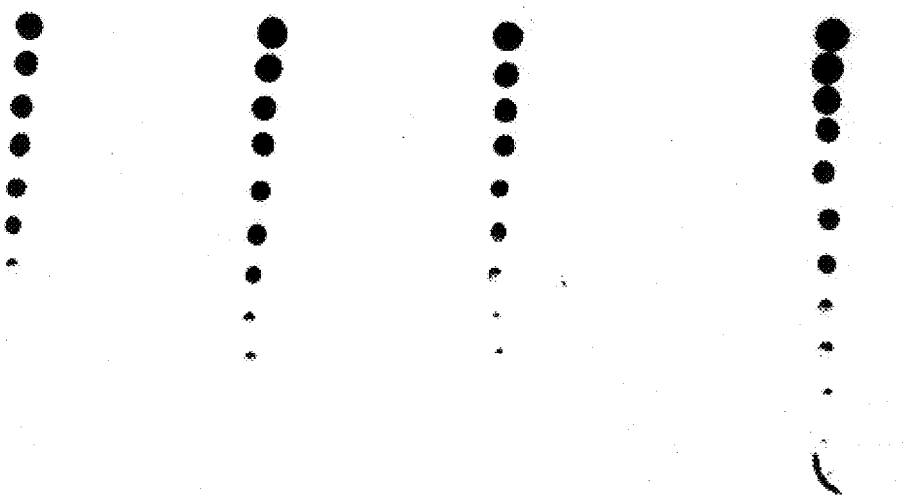
Figure 7A:
Figure 7B:
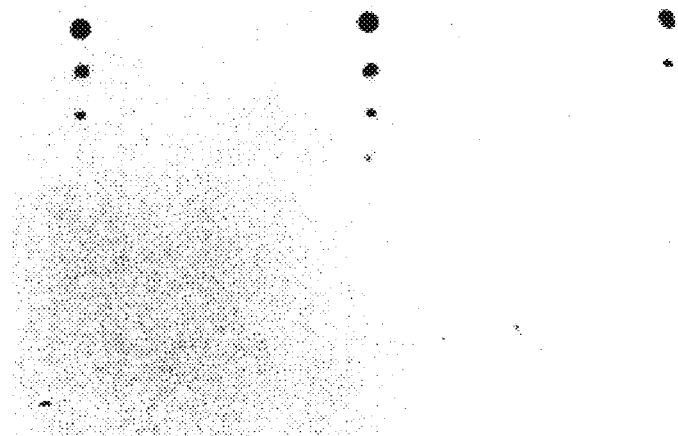
Figure 8A:
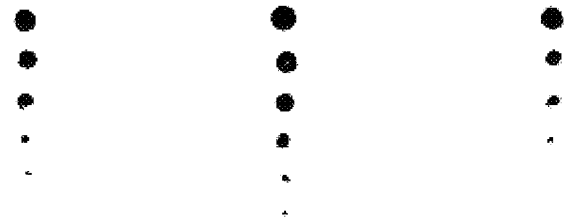
Figure 8B:
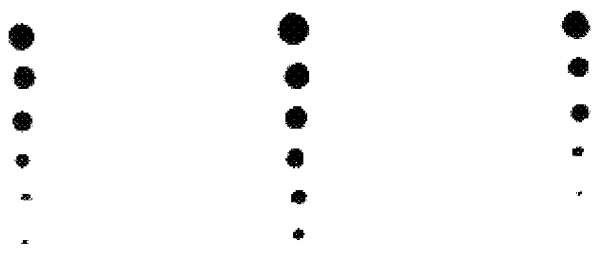
Figure 9A:
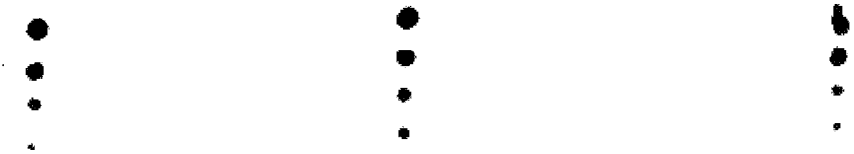
Figure 9B:
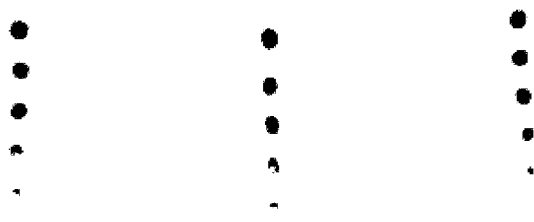
Figure 12A:
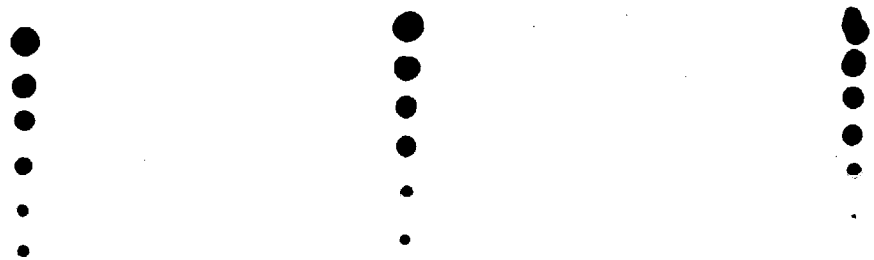
Figures 12B, 12C, 12D:
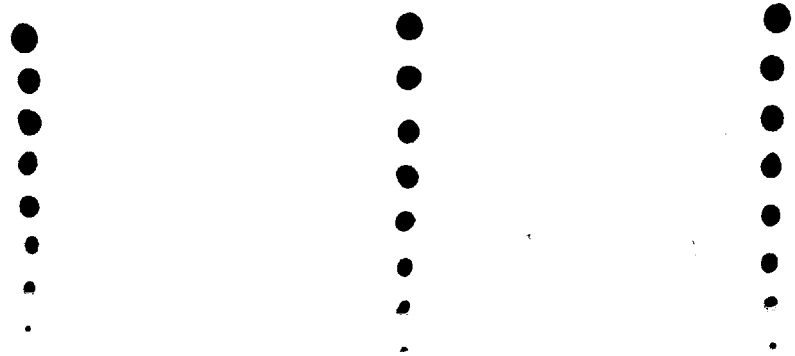

The dioxetanes of this invention are critically characterized by the substituents on the aromatic ring attached to the dioxetanes, which ring determines the electron transfer in the aryloxy anion, leading to decomposition and chemiluminescence. Thus, dioxetanes of the invention have the following and generalized structure (I).

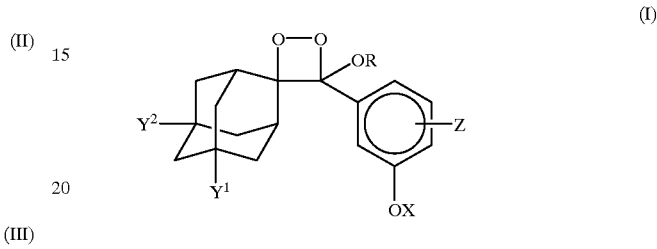

Thus, the adamantyl-stabilized dioxetanes of the claimed invention bear two substituents on the phenyl ring, as well as 0, 1 or 2 non-hydrogen substituents on the adamantyl ring. These substituents critically characterize the electronic characteristics of the dioxetane, the oxyanion, and its decomposition behavior. The identities of each substituent are set forth below.

R may by ally, aralkyl, cycloalkyl, or aryl, having 1–12 carbon atoms. R is preferably C1–C3 alkyl, most preferably, methyl. The identity of R may be optimized with regard to solubility concerns, where unusual analytes, or buffers, may pose particular problems. Each of $Y^1$ and $Y^2$ represent, individually, hydrogen, a hydroxyl group, a halo substituent, a hydroxy lower alkyl group, a halo lower alkyl group, a phenyl group, a halophenyl group, an alkoxy phenyl group, an alkoxy phenoxy group, a hydroxyalkoxy group, a cyano group, an amide group, a carboxyl group or substituted carboxyl group, an alkoxy group and other similar electron-active species. Preferred identities for $Y^1$ and $Y^2$ are chlorine, hydroxy, and methoxy.

X is an enzyme-cleavable moiety. Thus, upon proper contact with a suitable enzyme, X is cleaved from the molecule, leaving the oxygen attached to the phenyl ring, and thus, the phenoxy anion. X is ideally phosphate, galactoside, acetate, 1-phospho-2,3-diacylglyceride, 1-thio-D-glucoside, adenosine triphosphate, adenosine diphosphate, adenosine monophosphate, adenosine, α-D-glucoside, β-D-glucoside, β-D-glucuronide, α-D-mannoside, β-D-mannoside, β-D-fructofuranoside, β-glucosiduronate, P-toluenesulfonyl-L-arginine ester, and P-toluenesulfonyl-L-arginine amide. X is preferably phosphate or galactoside, most preferably phosphate. It is important to note that when substituted on the phenyl ring, OX is meta with respect to the point of attachment to the dioxetane ring, that is, it occupies the three position.

Z may occupy either the four or five position, most preferably the five position. Z is an electron-active substituent, the character of the electron-active species (electron-donating or electron-withdrawing), optimizing various aspects of the dioxetane moiety. As an example, an electron-donating group, such as a methoxy group, may enhance the dioxetane phenoxy anion decomposition process by facilitating the transferability of the free electrons from the aromatic ring O⁻ donor group to the dioxetane ring.

In contrast, an electron-withdrawing group would reduce or impair the ability to transfer the free electrons to the dioxetane, thus slowing the decomposition reaction and light emission, although ultimately giving a light signal of greater intensity. This should be contrasted with the impact of the electron-withdrawing substituent on the adamantyl group, such as chlorine, which substantially accelerates light emission, sharply reducing $T_{1/2}$. Of surprising significance is the fact that substitution in the six position is particularly undesirable. Such six-substituted phenyl dioxetanes exhibit extraordinarily fast decomposition kinetics, and nearly no light emission. While Applicants do not wish to be restricted to this theory, it is believed that this behavior is due to steric considerations, that is, the ortho substituent "turns" the phenyl ring such that it destabilizes the dioxetane ring (destabilization through steric forces, not electron transfer) and a substituent at the six position, e.g., methoxy, does not participate in electron transfer. As discussed below, experiments involving 6-substituted phenyl dioxetanes give essentially no signal.

The phenyl substituent on the dioxetane ring may instead by naphthyl (structures II and II) as

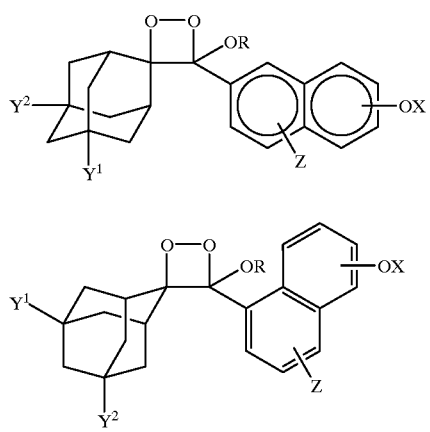

In the naphthyl dioxetane, identities for R, $Y^1$ and $Y^2$, X and Z remain the same. Instead of being restricted to the "meta" position, OX may occupy corresponding positions in the naphthyl ring, that is, non-conjugated positions, or positions such that the number of carbon atoms between the point of substitution and the point of attachment to the dioxetane ring, including the carbons at both point of attachment and point of substitution, are odd, as set forth in U.S. Pat. No. 4,952,707. Phenyl meta-substituted dioxetanes, and naphthyl dioxetanes substituted according to the pattern described above, may generally be expected to give higher quantum yields than the corresponding para and conjugated systems.

As noted above, Z can be any electron-active substituent that does not interfere with the chemiluminescent behavior of the dioxetane, and thus can be selected from a wide variety of identities. Preferred electron-active substituents include chloro, alkoxy (—OR), aryloxy (—OAr), trialkylammonium (—NR₃+), alkylamido (—NHCOR, —NRCOR'), arylamido (—NHCOAr, —NRCOAr, —NArCOAr), arylcarbamoyl (—NHCOOAr, —NRCOOAr), alkylcarbamoyl (—NHCOOR, —NRCOOR'), cyano (—CN), nitro (—NO₂), ester (—COOR, —COOAr), alkyl- or arylsulfonamido (—NHSO₂R, —NHSO₂Ar), trifluoromethyl (—CF₃), aryl (—Ar), alkyl (—R), trialkyl-, triaryl-, or alkylarylsilyl (—SiR₃, —SiAr₃, —SiArR₂), alkyl- or arylamidosulfonyl (—SO₂NHCOR, —SO₂NHCOAr), alkyl or aryl sulfonyl (—SO₂R, —SO₂Ar) alkyl- or arylthioethers (—SR, SAr). The size of the Z substituent is generally limited only by solubility concerns. Where reference is made to alkyl or R, R', etc., the alkyl moiety should have 1–12 carbon atoms. Suitable aryl moieties include phenyl and naphthyl as exemplary moieties. Particularly preferred species include chloro and alkoxy.

Dioxetanes of the type described above, without the inclusion of the Z substituent, as previously noted, are disclosed in patents commonly assigned herewith. Patents addressing dioxetanes of this type without the inclusion of the Y and Z substituents have also been assigned to Wayne State University, such as U.S. Pat. No. 4,962,192. Substitution of the Z substituent on the dioxetanes required development of the synthesis of trisubstituted phenyl phosphonates which is described below, under the title Novel Trisubstituted Phenyl 1,2-Dioxetane Phosphates. The same general synthesis route can be employed for naphthyl dioxetanes embraced herein, bearing in mind the substitution patterns required, as discussed above. The synthesis of these compounds through the route described below involves the preparation of novel tri-substituted benzenes. Thus, as described below, an exemplary compound involved in the synthesis of the dioxetanes of this class includes 3-chloro-5-methoxybenzaldehyde. These tri-substituted compounds constitute key intermediates in a variety of synthetic pathways, the 1,3,5 substitution pattern being a generally preferred and widely applicable pattern. It is Applicants' belief that these intermediates have never previously been prepared.

NOVEL TRI-SUBSTITUTED PHENYL 1,2-DIOXETANE PHOSPHATES

Synthesis

General

Commercial reagents were used as obtained without further purification. Baker silica gels (60–200 mesh for grain scale, and 230–400 mesh for milligram scale) were used for flash chromatography. ³¹P NMR spectra were reported in parts per million relative to a phosphoric acid standard. High resolution mass spectral analyses were run by J. L. Kachinski at Johns Hopkins University. Syntheses of dioxetanes 3 and 4 were carried out following the procedure described below for dioxetanes 1 and 2 respectively. Yields, melting points (uncorrected), and spectral data are summarized for isolated intermediates.

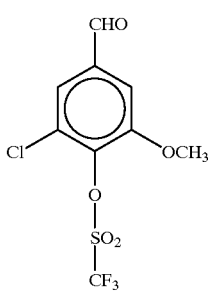

5

3-Chloro-5-methoxy-4-trifluoromethanesulfonyloxy Benzaldehyde (5)

A solution of 5-Cl-vanillin[1] (13.0 g, 70 mmol), chloroform (4 ml) and pyridine (16 ml) was stirred at 0° C. Addition of trifluoromethanesulfonic anhydride (12.4 ml, 75 mmol) at 0° C. over 30 min gave clean formation of the triflate. The reaction mixture was partitioned between EtOAc and 3N HCl, washed with dilute brine, dried over $Na_2SO_4$, and evaporated under reduced pressure. Purification of the resulting yellow oil by silica gel chromatography (30% EtOAc/hexanes) yielded 18.5 g (83%) triflate 5 as yellow crystals.

IR ($CHCl_3$, $cm^{-1}$): 1705, 1590, 1461, 1425, 1225, 1205, 1132, 1049, 875, 624

$^1$H NMR (ppm): 3.99 (3H, s), 7.44 (1H, d, J=1.6 Hz), 7.57 (1H, d, J=1.7 Hz), 9.92 (1H, s)

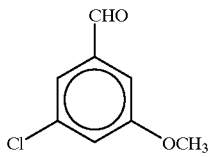

6

3-Chloro-5-methoxybenzaldehyde (6)

Triflate 5 (9 g, 28 mmol), palladium(II) acetate (120 mg, 0.5 mmol), 1,1'-bis(diphenylphosphino)ferrocene (620 mg, 1 mmol) and hplc grade $CH_3CN$ (10 ml) were mixed well in a teflon-lined stainless steel bomb. After adding freshly made, pulverized proton sponge formate$^2$ (7.84 g, 30 mmol), the bomb was sealed and heated at 90° C. for 4 h. The cooled reaction was then filtered to remove proton sponge crystals, partitioned between EtOAc and 3N HCl, washed once each with dilute brine and dilute $NaHCO_3$, dried over $Na_2SO_4$, and evaporated. Silica gel chromatography (15% EtOAc/hexanes) yielded 4.25 g (88.5%) of chloromethoxybenzaldehyde 6, mp 45° C.

IR ($CHCl_3$, $cm^{-1}$): 2835, 1700 (C=O), 1590, 1576, 1461, 1425, 1380, 1320, 1280, 1265, 1144, 1050, 850, 695

$^1$H NMR (ppm): 3.84 (3H, s), 7.13 (1H, m), 7.26 (1H, m), 7.41 (1H, m), 9.89 (1H, s)

Mass spectrum (EI, 70 eV): exact mass calcd for $C_8H_7ClO_2$ 170.0135, found 170.0134.

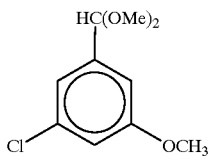

7

3-Chloro-5-methoxybenzaldehyde Dimethyl Acetal (7)

A methanol solution (20 ml) of benzaldehyde 6 (8.76 g, 51 mmol) was cleanly converted to dimethyl acetal 7 in the presence of trimethyl orthoformate (5.62 ml, 51 mmol) and a catalytic amount of p-toluenesulfonic acid. The reaction was quenched with triethylamine to pH 7, evaporated to a small volume and partitioned between EtOAc and $NaHCO_3$. The organic layer was dried, evaporated under reduced pressure and purified by silica gel chromatography (10% EtOAc/hexanes) to give 10.68 g (96%) of acetal 7 as a light yellow oil.

IR ($CHCl_3$, $cm^{-1}$): 2960, 2938, 2830, 1596, 1578, 1458, 1270, 1104, 1050, 989, 872, 865, 840

$^1$H NMR (ppm): 3.31 (6H, s), 3.79 (3H, s), 5.31 (1H, s), 6.85 (1H, s), 6.88 (1H, s), 7.04 (1H, s)

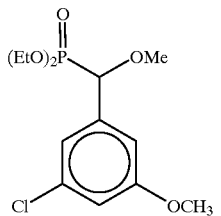

8

Diethyl 1-methoxy-1-(3-chloro-5-methoxyphenyl)methane Phosphonate 8

Triethyl phosphite (3.2 ml, 19 mmol) was added dropwise to a solution of acetal 7 (4.0 g, 18.5 mmol), boron trifluoride etherate (2.3 ml, 19 mmol) and $CH_2Cl_2$ (20 ml) at 0° C. After slowly warming the reaction to room temperature (30 min), the solution was partitioned with dilute $NaHCO_3$, dried over $Na_2SO_4$, evaporated and purified on silica gel (40%–100% EtOAc/hexanes) to give 4.6 g (77.5%) of phosphonate 8 as a light yellow oil.

IR ($CHCl_3$, $cm^{-1}$): 2990, 1591, 1573, 1458, 1254 (P=O), 1050 (P—O), 1025 (P—O), 969, 870, 687

$^1$H NMR (ppm): 1.24 (3H, t, J=7 Hz), 1.26 (3H, t, J=7 Hz), 3.37 (3H, s), 3.78 (3H, s), 4.01–4.09 (4H, m), 4.40 (1H, d, J=16 Hz), 6.83 (1H, t, J=2 Hz), 6.88 (1H, qt, J=2 Hz), 6.98 (1H, qt, J=2 Hz)

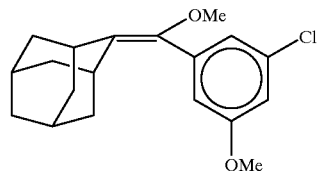

9

3-Chloro-5-methoxy-1-(methoxytricylo[3.3.1.1$^{3,7}$]-dec-2-ylidenemethyl)benzene (9)

Phosphonate 8 (4.62 g, 14 mmol) and 2-adamantanone (2.58 g, 17 mmol) were dissolved in anhydrous THF (35 ml) under argon and cooled to −68° C. Dropwise addition of lithium diisopropylamide (18.6 mmol) in anhydrous THF (20 ml) at −68° C. generated the ylid, followed by subsequent olefination of the ketone. The reaction was slowly warmed to room temperature over 2 h and then stirred at 75° C. for 1 h. The solution was partitioned between EtOAc/ $NH_4Cl$, dried over $Na_2SO_4$, evaporated and purified by silica gel chromatography (2% EtOAc/hexanes), yielding 2.5 g (55%) of enol ether 9 as an oil.

$^1$H NMR (ppm): 1.55–1.95 (12H, m), 2.61 (1H, br s), 3.21 (1H, br s), 3.28 (3H, s), 3.78 (3H, s), 6.74 (1H, s), 6.80 (1H, s), 6.87 (1H, s)

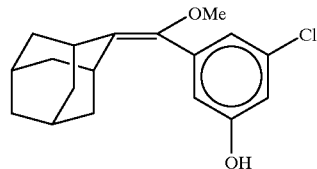

10

Chloro-5-hydroxy-1-(methoxytricyclo[3.3.1.1$^{3,7}$]-dec-2-ylidene-methyl)benzene (10)

Demethylation to enol ether phenol 10 proceeded cleanly upon heating enol ether 9 (2.5 g, 7.8 mmol) in DMF (14 ml)

at 155° C. in the presence of sodium ethane thiolate (11.7 mmol). Upon cooling, the mixture was partitioned between EtOAc and NH$_4$Cl, dried over Na$_2$SO$_4$ and evaporated under high vacuum to remove residual DMF. Chromatographic purification (silica gel, 20% EtOAc/hexanes) produced 2.3 g (96%) of phenol 10 as an oil which crystallized upon standing. Trituration of the solid with 5% EtOAc/hexanes gave white crystals, mp 133° C.

IR (CHCl$_3$, cm$^{-1}$): 3584 (OH), 3300 (OH), 2910, 1590, 1310, 1285, 1163, 1096, 1080, 1011, 900, 840

$^1$H NMR (ppm): 1.73–1.96 (12H, m), 2.62 (1H, br s), 3.20 (1H, br s), 3.32 (3H, s), 5.65 (1H, br s), 6.73 (1H, s), 6.79 (1H, m), 6.85 (1H, s)

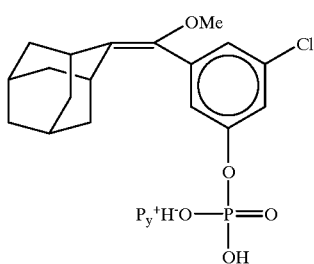

11

Pyridinium 3-chloro-5-(methoxytricyclo[3.3.1.1$^{3,7}$]-dec-2-ylidenemethyl)-1-phenyl Phosphate (11)

Triethylamine (450 μl, 3.2 mmol) was added under an argon atmosphere to enol ether 10 (709 mg, 2.3 mmol) dissolved in anhydrous THF (10 ml). The solution was cooled to 0° C., at which time 2-chloro-2-oxo-1,3,2-dioxaphospholane (Fluka, 285 μl, 3.0 mmol) was added dropwise. The reaction was warmed to room temperature, quickly passed through an argon-flushed column under inert atmosphere to remove triethylammonium hydrochloride crystals. After rinsing the crystal cake once with THF, the solution was evaporated and pumped dry to give crude phospholane 11a.

Opening the phospholane ring upon reaction of 11a with NaCN (vacuum dried, 179 mg, 3.65 mmol) in anhydrous DMF (6 ml) under argon, produced the desired β-cyanoethyl diester phosphate 11b, as well as regenerating enol ether phenol 10. Removal of DMF under high vacuum while warming the flask to 55° C., left a mixture of compounds 10 and 11b as a yellow-orange oil.

The above mixture was dissolved in methanol (8 ml) and stirred at 40° C. in the presence of NaOMe (1 ml of 4.25 M NaOMe/MeOH, 6.4 mmol), effecting β-elimination of the cyanoethyl group to give enol ether phosphate 11 as the disodium salt. After evaporating the methanol, the solid was dissolved in water and partitioned with minimal EtOAc to recover phenol 10 (333 mg). Purification of the aqueous phase by preparative HPLC, using a CH$_3$CN/H$_2$O gradient through a polystyrene column (PLRP-S, Polymer Laboratories), followed by ion exchange with pyridinium toluenesulfonate (Amberlyst-IR 120+resin) and lyophilization, yielded 448 mg (78% over 3 steps, accounting for recovered phenol) of enol ether phosphate 11 as a fluffy, off-white powder.

IR (CHCl$_3$, cm$^{-1}$): 2910, 1590, 1567, 1278, 1160, 1095, 945

$^1$H NMR (ppm): 1.73–1.96 (12H, m), 2.63 (1H, br s), 3.20 (1H, br s), 3.32 (3H, s), 5.89 (1H, s), 6.72 (1H, m), 6.79 (1H, t, J=2 Hz), 6.85 (1H, d, J=2 Hz)

$^{31}$P NMR (ppm): 54 (1P)

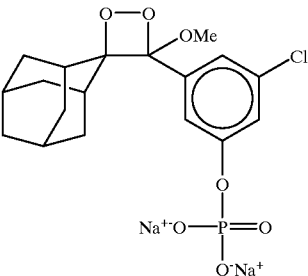

1

Disodium 3-chloro-5-(methoxyspiro(1,2-dioxetane-3,2'-tricylo[3.3.1.1$^{3,7}$]-decan]-4-yl)-1-phenyl Phosphate (1)

A solution of enol ether phosphate 11 and 5,10,15,20-tetraphenyl-21H,23H-porphine (TPP, 0.5 ml of a 2% solution in CHCl$_3$ by weight) in CHCl$_3$ (8 ml) was irradiated with a 250W, high pressure sodium lamp at 10° C. while passing a stream of oxygen through the solution. A 5-mil piece of Kapton polyimide film (DuPont) placed between the lamp and the reaction mixture filtered out unwanted UV radiation. Analytical HPLC (UV detector at 270 nm) showed complete dioxetane formation upon irradiating 5 min. After evaporation of the chloroform at 0° C., the residue was dissolved in ice water in the presence of Na$_2$CO$_3$ (27 mg, 0.25 mmol) and purified by preparative HPLC as described above. The fractions were frozen and lyophilized at 0° C., yielding 65.3 mg (90%) of dioxetane 1 as a fluffy white powder. TLC of the dioxetane exhibited blue chemiluminescence by thermal decomposition upon heating. Enzymatic cleavage of the phosphate also induced chemiluminescent decomposition in aqueous solutions.

$^1$H NMR (D$_2$O, ppm): 0.93 (1H, d, J=13 Hz), 1.21 (1H, d, J=13 Hz), 1.44–1.69 (10H, m) 2.16 (1H, br s), 2.78 (1H, br s), 3.14 (3H, s), 7.20 (2H, br s), 7.30 (1H, s)

$^{31}$P NMR (D$_2$O, ppm): 24 (1P)

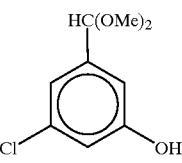

12

3-Chloro-5-hydroxy Benzaldehyde Dimethyl Acetal (12)

5-Chloro-3-methoxy benzaldehyde dimethyl acetal (7, 3.21 g, 14.8 mmol) was demethylated with sodium ethane thiolate (19 mmol) in DMF (14 ml) while heating at 150° C. The resultant phenol 12 was cooled, partitioned between EtOAc and NH$_4$Cl, dried over Na$_2$SO$_4$, evaporated and pumped to dryness on high vacuum to remove residual DMF. Chromatographic purification (silica gel, 20% EtOAc/hexanes) afforded 2.75 g (92%) of phenol 12 as a yellow oil. An analytical sample of the oil crystallized upon further purification, mp 153° C.

IR (CHCl$_3$, cm$^{-1}$): 3580 (OH), 3325 (OH), 2940, 2830, 1599, 1585, 1449, 1350, 1155, 1105, 1055, 894, 845

$^1$H NMR (ppm): 3.32 (6H, s), 5.30 (1H, s), 5.73 (1H, br s), 6.81 (2H, m), 7.01 (1H, s)

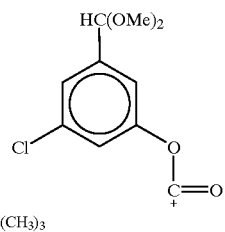

+ = C(CH₃)₃

3-Chloro-5-pivaloyloxybenzaldehyde Dimethyl Acetal (13)

Phenol 12 (2.7 g, 13.3 mmol) and triethylamine (2.8 ml, 20 mmol) in $CH_2Cl_2$ (20 ml) were stirred at 0° C. Addition of trimethylacetyl chloride (1.64 ml, 13.3 mmol) cleanly yielded the pivaloyl ester. Standard workup provided crude pivaloate 13 as an oil which was carried on to the next reaction without purification; no weight was taken. A small sample was purified by prep TLC for spectral characterization.

IR ($CHCl_3$, $cm^{-1}$): 2980, 2940, 1749 (C=O), 1585, 1448, 1349, 1250, 1150, 1109, 1056, 898

$^1$H NMR (ppm): 1.34 (9H, s), 3.31 (6H, s), 5.36 (1H, s), 7.06 (2H, br s), 7.31 (1H, s)

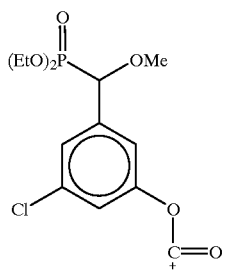

Diethyl 1-methoxy-1-(3-chloro-5-pivaloyloxyphenyl) methane Phosphonate (14)

A solution of acetal 13, boron trifluoride etherate (2.6 ml, 21 mmol) and $CH_2Cl_2$ (10 ml) was stirred at −78° C. Addition of triethyl phosphite (3.0 ml, 17.5 mmol) converted the acetal to phosphonate 14. Workup and purification (silica gel, 10% EtOAc/hexanes) yielded 2.43 g oil (47% over 2 steps).

IR ($CHCl_3$, $cm^{-1}$): 2995, 2980, 1750 (C=O), 1600, 1581, 1442, 1247 (P=O), 1110, 1028 (P—O), 975, 890

$^1$H NMR (ppm): 1.22–1.26 (6H, d of t, J=2 Hz, 7 Hz), 1.31 (9H, s), 3.39 (3H, s), 4.02–4.08 (4H, m), 4.44 (1H, d, J=16 Hz), 7.04 (2H, m), 7.27 (1H, br s)

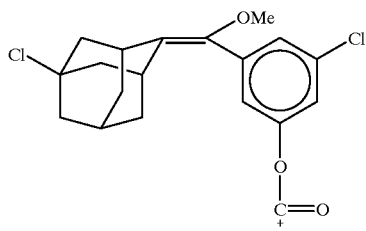

3-Chloro-5-pivaloyloxy-1-(methoxy-5-chloro-tricyclo [3.3.1.1$^{3,7}$]-dec-2-ylidenemethyl)benzene (15)

Phosphonate 14 (2.4 g, 6.1 mmol) was dissolved in anhydrous THF (10 ml) under argon and cooled to −68° C. Dropwise addition of lithium diisopropylamide (6.6 mmol) in anhydrous THF (7 ml) at low temperature generated the ylid, evident by deep coloration. After 5 min, a THF solution of 5-chloro-2-adamantanone (941 mg, 5 mmol) was added and the reaction was slowly warmed to room temperature over 40 min, followed by heating at 75° for 1 h to complete olefination. The solution was partitioned between EtOAc/$NH_4Cl$, dried over $Na_2SO_4$ and evaporated to give a crude mixture of enol ether pivaloate 15 and the corresponding enol ether phenol 16. The crude oil was used without purification in the following hydrolysis. A small sample was purified by prep TLC for spectral characterization.

IR ($CHCl_3$, $cm^{-1}$): 2935, 1750 (C=O), 1595, 1571, 1450, 1420, 1397, 1275, 1160, 1110, 1024, 918, 906, 887, 829

$^1$H NMR (ppm): 1.34 (9H, s), 1.68–1.78 (4H, m), 2.14–2.25 (7H, m), 2.77 (1H, br s), 3.30 (3H, s), 3.42 (1H, br s), 6.88 (1H, d, J=1.5 Hz), 7.04 (1H, m), 7.11 (1H, d, J=1.5 Hz)

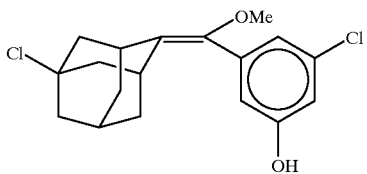

3-Chloro-5-hydroxy-1-(methoxy-5-chloro-tricyclo [3.3.1.1$^{3,7}$]-dec-2-ylidenemethyl)benzene (16)

Crude pivaloate 15 was hydrolyzed at room temperature with $K_2CO_3$ (1.45 g, 10.5 mmol) in 10 ml methanol. Evaporation of methanol, followed by standard workup and purification (silica gel, 30% EtOAc/hexanes) afforded 1.095 g (63% over 2 steps) of a slightly yellow oil which solidified upon standing. Trituration of the solid produced white crystalline enol ether phenol 16, mp 130° C.

IR ($CHCl_3$, $cm^{-1}$): 3590 (OH), 3300 (OH), 2935, 1595, 1163, 1100, 1082, 1030, 911

$^1$H NMR (ppm): 1.69–1.83 (4H, m), 2.14–2.27 (7H, m), 2.77 (1H, br s), 3.30 (3H, s), 3.41 (1H, br s), 5.21 (1H, br s), 6.67 (1H, d, J=1.5 Hz), 6.81 (1H, m), 6.84 (1H, d)

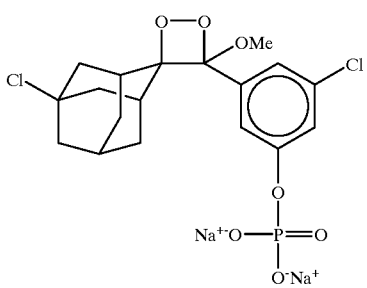

Disodium 3-chloro-5-(methoxyspiro(1,2-dioxetane-3,2'-(5-chloro-)tricyclo-[3.3.1.1$^{3,7}$]-decan]-4-yl)-1-phenyl Phosphate (2)

Triethylamine (230 μl, 1.65 mmol) was added under an argon atmosphere to enol ether 16 (356 mg, 1.05 mmol) dissolved in anhydrous THF (5 ml). The solution was cooled to 0° C., at which time 2-chloro-2-oxo-1,3,2-dioxaphospholane (Fluka, 143 μl, 1.55 mmol) was added dropwise. The reaction was warmed to room temperature and quickly passed through an argon-flushed column under inert atmosphere to remove triethylammonium hydrochloride crystals. After rinsing the crystal cake once with THF, the solution was evaporated and pumped dry to give crude pholane 17a.

Opening the phospholane ring upon reaction with NaCN (vacuum dried, 69 mg, 1.4 mmol) in anhydrous DMF (5 ml) under argon, produced the desired β-cyanoethyl diester phosphate 17b. Removal of DMF under high vacuum while warming the flask to 55° C. left the crude diester phosphate as an orange oil.

A solution of cyanoethyl phosphate 17b and 5,10,15,20-tetraphenyl-21H,23H-porphine (TPP, 1.5 ml of a 2% solution in CHCl₃ by weight) in CHCl₃ (10 ml) was irradiated with a 250 W, high pressure sodium lamp at 10° C. while passing a stream of oxygen through the solution. A 5-mil piece of Kapton polyimide film (DuPont) placed between the lamp and the reaction mixture filtered out unwanted UV radiation. Analytical HPLC (UV detector at 270 nm) showed complete dioxetane formation upon irradiating 15 min. After evaporation of the chloroform at 0° C., the residue was dissolved in methanol and deprotected to the disodium phosphate dioxetane with NaOMe (0.5 ml of 4.25 M NaOMe/MeOH, 2 mmol). Upon β-elimination of the cyanoethyl group, the solvent was evaporated at 0° and the residue dissolved in ice water. Purification by preparative HPLC, as described above, followed by lyophilization at 0° C., yielded 289 mg (60% over 4 steps) of dioxetane 2 as a fluffy white powder.

$^1$H NMR (D$_2$O, ppm, mixture of syn/anti isomers): 0.86 (1H, d), 1.13 (1H, d, J=14 Hz), 1.30 (1H, d), 1.37 (1H, d), 1.45–2.07 (18H, m), 2.27 (1H, br s), 2.32 (1H, br s), 2.95 (2H, br s), 3.09 (3H, s), 3.11 (3H, s), 7.0–7.3 (4H, br s), 7.25 (1H, s), 7.28 (1H, s)

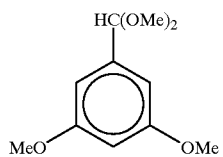

18

3,5-Dimethoxybenzaldehyde Dimethyl Acetal (18)

IR (CHCl₃, cm$^{-1}$): 2958, 2935, 1598, 1460, 1426, 1357, 1190, 1154, 1101, 1053, 840

$^1$H NMR (ppm): 3.32 (6H, s), 3.78 (6H, s), 5.28 (1H, s), 6.41 (1H, m), 6.60 (2H, m)

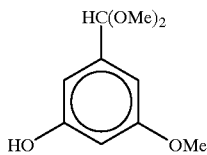

19

3-Hydroxy-5-methoxybenzaldehyde Dimethyl Acetal (19)

IR (CHCl₃, cm$^{-1}$): 3590 (OH), 3345 (OH), 2940, 2830, 1600, 1462, 1432, 1355, 1190, 1150, 1110, 1055, 841

$^1$H NMR (ppm): 3.32 (6H, s), 3.77 (3H, s), 5.28 (1H, s), 6.37 (1H, d, J=2 Hz), 6.53 (1H, br s), 6.58 (1H, br s)

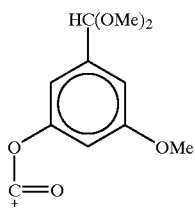

20

3-Methoxy-5-pivaloyloxybenzaldehyde Dimethyl Acetal (20)

(73% Over 3 Steps, Oil)

IR (CHCl₃, cm$^{-1}$): 2960, 2935, 1741 (C=O), 1608, 1597, 1462, 1350, 1273, 1190, 1139, 1115, 1056, 999, 902, 848

$^1$H NMR (ppm): 1.34 (9H, s), 3.31 (6H, s), 3.80 (3H, s), 5.35 (1H, s), 6.57 (1H, d, J=2 Hz), 6.75 (1H, br s), 6.87 (1H, br s)

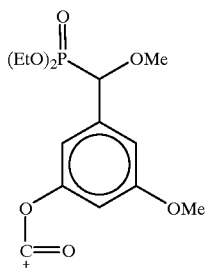

21

Diethyl 1-methoxy-1-(3-methoxy-5-pivaloyloxyphenyl)methane Phosphonate (21)

(40% Oil)

IR (CHCl₃, cm$^{-1}$): 2990, 2980, 1742 (C=O), 1606, 1590, 1463, 1272, 1240, 1136, 1110, 1100, 1055, 1023, 970

$^1$H NMR (ppm): 1.21 (3H, t, J=3 Hz), 1.23 (3H, t), 1.32 (9H, s), 3.39 (3H, s), 3.78 (3H, s), 4.06 (4H, m), 4.44 (1H, d, J=16 Hz), 6.56 (1H, m), 6.72 (1H, m), 6.85 (1H, m)

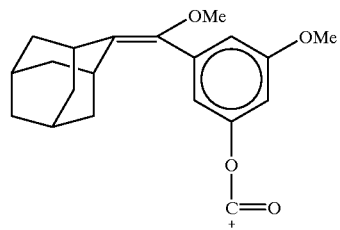

22a

3-Methoxy-5-pivaloyloxy-1-(methoxytricyclo[3.3.1.1$^{3,7}$]-dec-2-ylidenemethyl)benzene (22a)

IR (CHCl₃cm$^{-1}$) 2910, 1740 (C=O), 1600, 1580, 1460, 1325, 1272, 1140, 1114, 1097, 1079, 1055

$^1$H NMR (ppm): 1.35 (9H, s), 1.56–1.96 (12H, m), 2.68 (1H, br s), 3.23 (1H, br s), 3.31 (3H, s), 3.80 (3H, s), 6.53 (1H, t, J=2 Hz), 6.61 (1H, br s), 6.72 (1H, m)

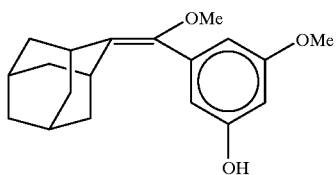

22

3-Hydroxy-5-methoxy-1-(methoxytricyclo[3.3.1.1³,⁷]-dec-2-ylidenemethyl)benzene (22a) (64%, White Crystals, mp 159° C.

IR (CHCl₃, cm⁻¹): 3590 (OH), 3320 (OH), 2910, 1591, 1342, 1150, 1098

¹H NMR (ppm): 1.78–1.97 (12H, m), 2.68 (1H, br s), 3.23 (1H, br s), 3.33 (3H, s), 3.78 (3H, s), 5.49 (1H, s), 6.37 (1H, m), 6.45 (2H, m)

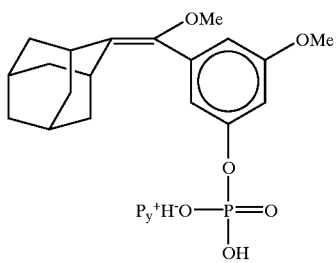

23

Pyridinium 5-methoxy-3-(methoxytricyclo[3.3.1.1³,⁷]-dec-2-ylidenemethyl)-1-phenyl Phosphate (23) (62%, Off-white Fluffy Powder).

IR (CHCl₃, cm⁻¹): 2911, 1584, 1448, 1425, 1328, 1149, 1099, 960, 870

¹H NMR (ppm): 1.68–1.92 (12H, m), 2.63 (1H, br s), 3.17 (1H, br s), 3.23 (3H, s), 3.68 (3H, s), 6.55 (1H, br s), 6.72 (1H, br s), 6.76 (1H, br s), 6.98 (1H, br s)

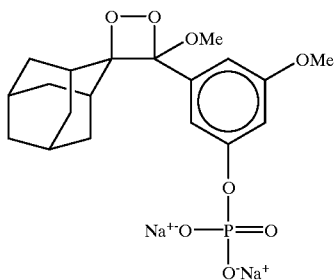

3

Disodium 5-methoxy-3-(methoxyspiro(1,2-dioxetane-3,2'-tricyclo[3.3.1.1³,⁷]-decan]-4-yl)-1-phenyl Phosphate (3)

(85%, White Fluffy Powder)

¹H NMR (D₂O, ppm): 0.98 (1H, br d), 1.22 (1H, br d), 1.46–1.76 (10H, m), 2.20)1H, br s), 2.78 (1H, br s), 3.14 (3H, s), 3.74 (3H, s), 6.91 (1H, br s), 6.68–6.97 (2H, very broad signal) ³¹P NMR (D₂O, ppm): 44.8 (1P)

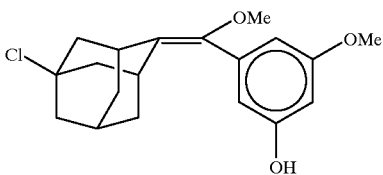

24

3-Hydroxy-5-methoxy-1-(methoxy-5-chloro-tricyclo[3.3.1.1³,⁷]-dec-2-ylidenemethyl)benzene (24)

(63%, White Crystals, mp 134° C.)

IR (CHCl₃, cm⁻¹): 3590 (OH), 3330 (OH), 2930, 1610, 1591, 1450, 1430, 1341, 1150, 1100, 1080, 1056, 1028, 829

¹H NMR (ppm): 1.68–2.40 (11H, m), 2.82 (1H, br s), 3.31 (3H, s), 3.42 (1H, br s), 3.78 (3H, s), 6.37–6.41 (3H, m)

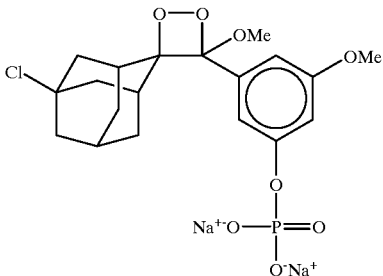

4

Disodium 5-methoxy-3-(methoxyspiro(1,2-dioxetane-3,2'-(5-chloro-)tricyclo-[3.3.1.1³,⁷]-decan]-4-yl)-1-phenyl Phosphate (4)

(57% Over 4 Steps, White Fluffy Powder)

¹H NMR (D₂O, ppm, mixture of syn/anti isomers): 0.94 (1H, br d), 1.19 (1H, br d), 1.42 (1H, br d), 1.50 (1H, br s), 1.58 (1H, br d), 1.67–2.16 (17H, m), 2.38 (1H, br s), 2.40 (1H, br s), 3.00 (2H, br s), 3.15 (3H, s), 3.16 (3H, s), 3.73 (3H, s), 3.74 (3H, s), 6.90 (1H, br s) 6.93 (1H, br s), 6.65–7.00 (4H, very broad signal)

³¹P NMR (D₂O, ppm, mixture of syn/anti isomers): 44.8 (2P)

REFERENCES 1. 5-Chlorovanillin was synthesized as described by Hann and Spencer (J. Am. Chem. Soc., 1927, 49:535–537), mp 163° C.

2. Proton sponge formate (N,N,N',N',-tetramethyl-1,8-naphthalenediammonium formate): Formic acid (98%, 1.2 ml, 31 mmol) was added to a solution of proton sponge (6.8 g, 32 mmol) and CH₂Cl₂ (8 ml) at 0° C. After warming to room temperature, the solvent was evaporated and the proton sponge formate crystallized as white crystals while drying on high vacuum with minimal warming. Proton sponge formate crystals (mp 79° C.) must be used soon after preparation since formic acid will evaporate upon standing, leaving proton sponge (mp 50° C.).

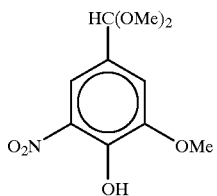

25

3-Methoxy-5-nitro-4-hydroxy Benzaldehyde Dimethyl Acetal (25)

A methanol solution (30 ml) of 5-nitrovanillin (5.0 g, 97%, 18.4 mmol) was cleanly converted to dimethyl acetal 25 in the presence of trimethyl orthoformate (2.8 ml, 25 mmol) and a catalytic amount of p-toluenesulfonic acid. The reaction was quenched with triethylamine to pH 8, evaporated to a small volume and partitioned between EtOAc and NaHCO$_3$. The aqueous layer was washed once with EtOAc. The organic layers were dried over Na$_2$SO$_4$, decanted and evaporated to an orange-red oil that crystallized upon pumping. Recrystallization from 50% EtOAc/hexanes gave 5.55 g (93%) acetal 25 as red-orange crystals, mp 58–59° C.

IR (CHCl$_3$, cm$^{-1}$): 3300, 3010, 2930, 2820, 1620, 1543, 1460, 1445, 1392, 1341, 1320, 1254, 1132, 1101, 1058, 990, 865

$^1$H NMR (ppm): 3.31 (6H, s), 3.94 (3H, s), 5.31 (1H, s), 7.22 (1H, d, J=1.7 Hz), 7.78 (1H, d)

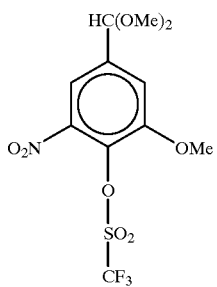

26

3-Methoxy-5-nitro-4-trifluoromethanesulfonyloxy Benzaldehyde Dimethyl Acetal (26)

A solution of dimethyl acetal 25 (5.0 g, 20.6 mmol), chloroform (3 ml) and pyridine (8 ml) was stirred at 0° C. under argon. Addition of trifluoromethanesulfonic anhydride (4.0 ml, 23.8 mmol) at 0° C. over 10 min, followed by stirring at room temperature overnight gave clean formation of the triflate. The solvents were evaporated under high vacuum while warming the oil to 45° C. and traces of pyridine were chased with 4 ml toluene. The resulting oil was pumped well under high vacuum, taken up in 50% EtOAc/hexanes and triturated with 50% EtOAc/hexanes to separate the desired triflate (in solution) from the fine pyridinium triflate crystals. Evaporation of the trituration solution, followed by purification of the oil on a silica gel column, eluting with 30% EtOAc/hexanes, yielded 6.43 g (84%) of triflate 26 as a light yellow oil.

IR (CHCl$_3$, cm$^{-1}$):

$^1$H NMR (ppm): 3.35 (6H, s), 4.00 (3H, s), 5.42 (1H, s), 7.42 (1H, d, J=1.6 Hz), 7.73 (1H, d)

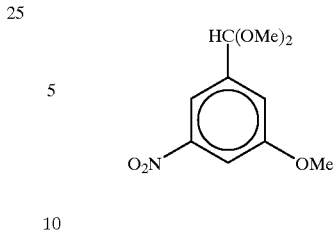

27

3-Methoxy-5-nitro-benzaldehyde Dimethyl Acetal (27)

5-Nitrophenyl triflate 26 (7 g, 18.7 mmol), palladium (II) acetate (88 mg, 0.39 mmol), 1,1'-bis(diphenylphosphino)ferrocene (430 mg, 0.78 mmol) and hplc grade CH$_3$CN (10 ml) were mixed well in a teflon-lined stainless steel bomb. After adding freshly made, pulverized proton sponge formate (5.1 g, 19.6 mmol), the bomb was sealed and heated at 90° C. for 2 h. The reaction mixture was taken up in EtOAc, passed through a silica gel plug, and then purified on a silica gel column, eluting with 0–30% EtOAc/hexanes to yield 1.5 g (35%) methoxynitrobenzaldehyde acetal 27.

IR (CHCl$_3$, cm$^{-1}$): 3005, 2960, 2935, 2835, 1532 (—NO$_2$), 1463, 1450, 1343 (—NO$_2$), 1280, 1190, 1158, 1104, 1055, 990, 871

$^1$H NMR (ppm): 3.33 (6H, s), 3.89 (3H, s), 5.41 (1H, s), 7.33 (1H, s), 7.68 (1H, s), 7.92 (1H, s)

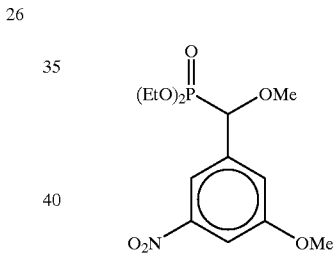

28

Diethyl 1-methoxy-1-(3-methoxy-5-nitrophenyl)methane Phosphonate (28)

Triethyl phosphite (0.98 ml, 5.7 mmol) was added dropwise to a solution of dimethyl acetal 27 (1.08 g, 4.7 mmol), boron trifluoride etherate (1.2 ml, 9.8 mmol) and CH$_2$Cl$_2$ (10) at 0° C. After warming the reaction to room temperature overnight, the solution was partitioned with 3N HCl and the aqueous layer was washed with CH$_2$Cl$_2$ twice. The organic layers were washed with dilute NaHCO$_3$, dried over Na$_2$SO$_4$, decanted and evaporated. The crude residue was purified on a silica gel column, eluting with 0–80% EtOAc/hexanes, to give 1.36 g (86%) phosphonate 28 as a slightly yellow oil.

IR (CHCl$_3$, cm$^{-1}$): 2995, 1532 (—NO$_2$), 1350 (—NO2), 1280, 1258, 1243, 1096, 1053, 1025, 973, 721

$^1$H NMR (ppm): 1.28 (6H, t, J=7.1 Hz), 3.44 (3H, s), 3.90 (3H, s), 4.08–4.15 (4H, m), 4.55 (1H, d, J=16 Hz), 7.34 (1H, d), 7.69 (1H, d, J=2.1 Hz), 7.87 (1H, d, J=1.6 Hz)

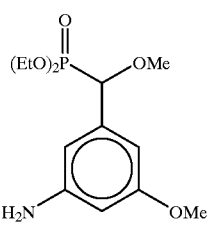

29

Diethyl 1-methoxy-1-(3amino-5-methoxyphenyl)methane Phosphonate (29)

Nitro phosphonate 28 is dissolved in methylene chloride and added to a 1M NaOH solution containing $nBu_4NBr$ and sodium hydrosulfite. The biphasic solution is stirred vigorously, with warming if necessary, until reduction of the nitro substituent to aniline 29 is complete. The cooled solution is partitioned between $CH_2Cl_2$ and minimal water, and the aqueous layer is washed with $CH_2Cl_2$ as needed to obtain the crude aniline. The combined organic layers are dried, decanted and evaporated. The residue is then passed through a short silica gel plug to give aniline 29.

IR ($CHCl_3$, $cm^{-1}$):
$^1$H NMR (ppm):
(References for other reduction conditions are appended to the synthesis summary.)

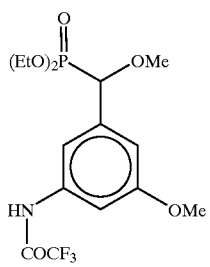

30

Diethyl 1-methoxy-1-(3-methoxy-5-trifluoroacetamidophenyl)methane Phosphonate (30)

Phosphonate 29 is quantitatively acetylated by addition of trifluoroacetic anhydride (1 eq) and triethylamine (1.3 eq) in 10 ml $CH_2Cl_2$ at 0° C. Evaporation of solvents, followed by silica gel column purification yields trifluoroacetamide 30.

IR ($CHCl_3$, $cm^{-1}$):
$^1$H NMR (ppm):

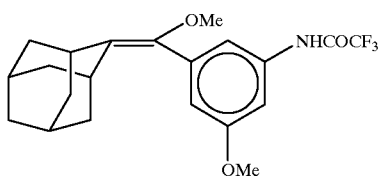

31

3-Methoxy-5-trifluoroacetamido-1-(methoxytricyclo[$3.3.1.1^{3,7}$]-dec-2-ylidenemethyl)benzene (31)

Phosphonate 30, dissolved in anhydrous THF, is cooled to −68° C. under an argon atmosphere. Similarly, 2-adamantanone (1.1 eq) is dissolved in anhydrous THF and cooled to −68° C. under argon in a separate flask. To the phosphonate solution is added 2.5M nBuLi at −68° C. under argon until the red color of the ylid persists. At this point, 1.2 eq nBuLi is added to complete the ylid formation and the resulting colored solution is stirred at −68° C. for 5 min. While maintaining the low temperature, 2-adamantanone in THF is slowly added to the ylid over an hour. After the final addition of ketone, the reaction mixture is stirred for 2 h while warming to room temperature. The reaction is then heated at reflux for 1 h, cooled and quenched by partitioning with EtOAc and saturated $NH_4Cl$. The organic layer is dried over $Na_2SO_4$ and chromatographed with EtOAc/hexanes on a silica gel column to give enol ether 31.

IR ($CHCl_3$, $cm^{-1}$):
$^1$H NMR (ppm):

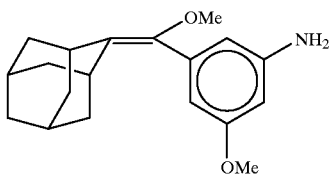

32

3-Amino-5-methoxy-1-(methoxytricyclo[$3.3.1.1^{3,7}$]-dec-2-ylidenemethyl)benzene (32)

Trifluoroacetamide enol ether 31 is hydrolyzed at 60° C. with finely ground $K_2CO_2$ (3 eq) in MeOH containing trace water. Workup by partitioning the mixture with EtOAc/$H_2O$, followed by silica gel chromatography provides enol ether aniline 32.

IR ($CHCl_3$, $cm^{-1}$):
$^1$H NMR (ppm):

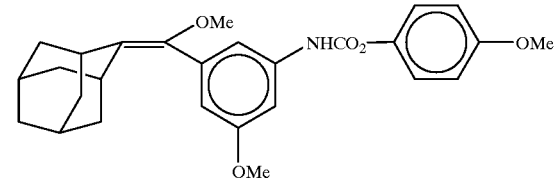

33

3-Carbamoyl-5-methoxy Derivatives (3-NHCO$_2$X)
3-para-Methoxyphenylcarbamoyl-5-methoxy-1-(methoxytricyclo[$3.3.1.1^{3,7}$]-dec-2-ylidenemethyl)benzene (33)

Enol ether aniline 32 in methylene chloride is carboxylated with 4-methoxyphenyl chloroformate (1.1 eq) in the presence of triethylamine (2.0 eq) at 0° C. The reaction mixture is partitioned with $CH_2Cl_2/H_2O$, washed with dilute $NaHCO_3$, dried over $Na_2SO_4$, evaporated and chromatographed on silica gel to yield enol ether p-methoxyphenylcarbamate 33.

IR ($CHCl_3$, $cm^{-1}$):
$^1$H NMR (ppm):

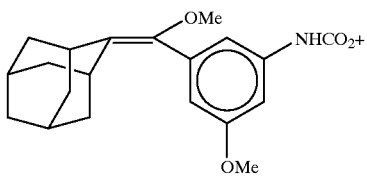

34

3-tert-Butylcarbamoyl-5-methoxy-1-(methoxytricyclo[$3.3.1.1^{3,7}$]-dec-2-ylidenemethyl)benzene (34)

A methylene chloride solution of enol ether aniline 32, triethylamine (1.5 eq) and BOC-On (1.3 eq) is stirred at 55° C. in a tightly capped Kimax tube to effect t-butyl carbamate formation. The solution is cooled, evaporated to a small volume and, upon addition of MeOH to the residue, the desired carbamate 34 precipitates.

IR (CHCl$_3$, cm$^{-1}$):
$^1$NMR (ppm):

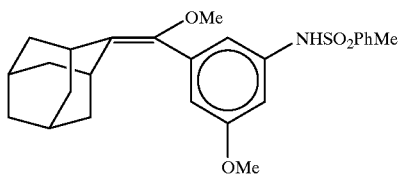

35

3-N-Sulfonamido-5-methoxy Derivatives (3-NHSO$_2$X)
3-N-Toluenesulfonamido-5-methoxy-1-(methoxytricyclo [3.3.1.1$^{3,7}$]-dec-2-ylidenemethyl)benzene (35)

A methylene chloride solution of enol ether aniline 32 is sulfonylated with tosyl chloride (1.1 eq) in the presence of triethylamine (2.0 eq) at 0° C. The reaction mixture is partitioned with CH$_2$Cl$_2$/H$_2$O, washed with dilute NaHCO$_3$, dried over Na$_2$SO$_4$, evaporated and chromatographed on silica gel to yield N-toluenesulfonamido enol ether 35.

IR (CHCl$_3$, cm$^{-1}$)
$^1$H NMR (ppm):

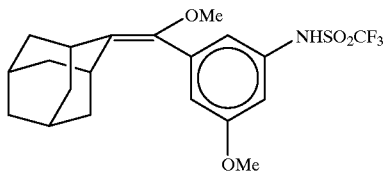

36

3-N-Trifluoromethylsulfonamido-5-methoxy-1-(methoxytricyclo[3.3.1.1$^{3,7}$]-dec-2-ylidenemethyl)benzene (36)

A methylene chloride solution of enol ether aniline 32 is sulfonylated with trifluoromethylsulfonyl anhydride (1.1 eq) at 0° C. The reaction mixture is partitioned with CH$_2$Cl$_2$/H$_2$O, dried over Na$_2$SO$_4$, evaporated and chromatographed on silica gel to yield N-trifluoromethylsulfonamido enol ether 36.

IR (CHCl$_3$, cm$^{-1}$):
$^1$NMR (ppm):

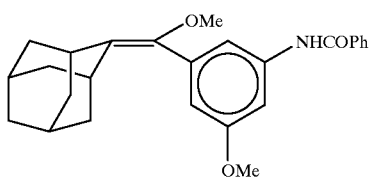

37

3-Amido-5-methoxy Derivatives (3-NHCOX)
3-N-Benzamido-5-methoxy-1-(methoxytricyclo[3.3.1.1$^{3,7}$]-dec-2-ylidenemethyl)benzene (37)

A pyridine solution of enol ether aniline 32 is reacted with benzoyl chloride (1.1 eq) at 0° C. The solvent is evaporated and pumped well to yield a crude oil, which is partitioned between CH$_2$Cl$_2$/H$_2$O, dried and evaporated. Chromatography on silica gel yields benzamido enol ether 37.

IR (CHCl$_3$, cm$^{-1}$):
$^1$H NMR (ppm):

The 3-nitrogen-substituted phenyl enol ethers (compounds 33–37) are demethylated with sodium ethane thiolate, and then phosphorylated and photooxygenated as described for dioxetanes 1 and 2 to obtain the analogous dioxetanes.

EXAMPLES

Various dioxetanes within the scope of this invention have been prepared and tested for essential properties, such as quantum yield (performed by an independent laboratory according to the procedure listed below), T$_{1/2}$ and the emission wavelength maxima. These dioxetanes are identified by number, and in the tables following after the number, the identity of the substituent on the adamantyl ring, if any followed by the identity of the Z substituent is given. In the compounds tested, X is phosphate. Values for quantum yield and T$_{1/2}$ are obtained both for the dioxetane along in 0.1 molar DEA, and in the presence of an enhancement agent, Sapphire II.

Protocol for Quantum Yields Determination

500 µL of 3.2×10$^{-4}$M solution of a dioxetane in 0.1M Na$_2$CO$_3$, pH 9.5 was placed in a 12×75 mm tube, at 20° C. The solution was equilibrated to 20° C. in a refrigerated water bath for 10 minutes. 2 µL of alkaline phosphatase suspension was added to the tube containing dioxetane and immediately vortexed for 1 sec and placed in the 20° C. water bath. The tube was then placed in MGM Optocomp® I luminometer and the light signal was measured at 1 sec integration times. After the light signal was measured, the tube was placed back into the 20° C. water bath and the measurement was repeated. The total counts for the dioxetane were determined from the intensity data. Total counts observed for a given concentration of dioxetane is the product of Photon Detection Efficiency (PDE) of the luminometer, the quantum yield of dioxetane and the number of molecules capable of emitting light (concentration of dephosphorylated dioxetanes). PDE for the MGM Optocomp® I luminometer was determined to be 2.56×10$^{-3}$, measured with a Biolink® absolute standard and utilizing the known spectral response of the luminometer's PMT and the known emission spectrum of the dioxetanes. The quantum yield is calculated by dividing the total counts measured by the PDE and the concentration of the dioxetane.

Calculation of Half Life or Half Time to Steady State Light Emission

From the Turner luminometer readout, the maximum signal was measured. The maximum signal minus the Turner light unit readings at 30, 150, 300, or 600 second intervals was calculated and graphed vs. time in seconds. From the graphs, an exponential equation was calculated to determine the half life.

The half lives of the dioxetanes were also determined directly from the Turner X luminometer printouts.

Emission Maxima

To 2 ml of a pH 10 solution of 0.4 mM dioxetane, 0.1 M diethanolamine, 1 mM MgCl$_2$ was added 9.9×10$^{-11}$M alkaline phosphatase. The solution was equilibrated 5 minutes in a Spex Fluorolog Fluorimeter and then scanned 5 times at 0.5 sec/nm for chemiluminescent emission. The chemiluminescence emission wavelength maximum was recorded.

Chemiluminescent DNA Sequencing

DNA sequencing with chemiluminescent detection was performed as described in the Tropix SEQ-Light™ protocol. Briefly, DNA sequencing reactions were initiated with biotinylated primers using M13 single stranded phage DNA as a template. The reactions were separated by 8 M urea denaturing PAGE, transferred horizontally to Tropilon-Plus nylon membrane by capillary action, and cross-linked to the membrane by exposure to UV light using a Spectronics SpectroLinker XL-1500 at 200 mJ/cm². The membranes were incubated with blocking buffer (0.2% I-Block™, 0.5% sodium, dodecyl sulphate/SDS, in phosphate buffered saline/PBS [20 mM sodium phosphate, pH 7.2, 150 mM NaCl]) for 10 minutes, incubated with a 1/5000 dilution of Avidx-AP streptavidin-alkaline phosphatase in blocking buffer for 20 minutes, washed for 5 minutes in blocking buffer, washed 3×5 minutes with wash buffer (0.5% SDS, PBS), washed 2×5 minutes with assay buffer (0.1 M diethanolamine, 1 mM $MgCl_2$ pH 10), and then incubated with dioxetane solution (either CSPD, 140-17 or 128-87 diluted to 0.25 mM in assay buffer) for 5 minutes. The membranes were drained, sealed in a plastic folder and exposed to Kodak XAR-5 x-ray film. For the dioxetane 128-87, the exposure time was 70 minutes and for 140-17, 80 minutes, both 65 minutes after substrate addition. For the comparison of dioxetane 128-87 versus CSPD, the membrane exposure time was 5 minutes after a 24 hour incubation with substrate. The details of this type of protocol are reflected in Topix SEQ-Light™ DNA sequencing system, commercially available from Tropix, Inc.

| 0.1M DEA, pH, 25° C. Dioxetane concentration $3.7 \times 10^{-7}$M to $6 \times 10^{-6}$M | | | |
|---|---|---|---|
| Compound | Quantum Yield | T ½ (min) | μL em |
| 128-70 (H, 5-Cl) | $1.4 \times 10^{-4}$ | 35.55 | 471 |
| 128-87 (Cl, 5-Cl) | $1.2 \times 10^{-4}$ | 9.03 | 470 |
| 140-20 (H, 5-OMe) | $1.5 \times 10^{-5}$ | 1.55 | 476 |
| 140-17 (Cl, 5-OMe) | $2.3 \times 10^{-5}$ | 1.09 | 475 |
| 140-62 (H, 6-OMe) | $1.1 \times 10^{-6}$ | 2.4 | 490 |
| 140-73 (Cl, 6-OMe) | $6.8 \times 10^{-7}$ | 2.0 | 487 |
| AMPPD | $1.5 \times 10^{-5}$ | 2.1 | 477 |
| CSPD | $5.2 \times 10^{-5}$ | 1.6 | 475 |

| 0.09M DEA + 0.1% Sapphire II, pH 9.95, 25° C. Dioxetane concentration $1.8 \times 10^{-7}$M to $6.1 \times 10^{-9}$M | | |
|---|---|---|
| Compound | Quantum Yield | T ½ (min) |
| 128-70 (H, 5-Cl) | $5.2 \times 10^{-2}$ | 172 |
| 128-87 (Cl, 5-Cl) | $3.5 \times 10^{-2}$ | 70.6 |
| 140-20 (H, 5-OMe) | $2.4 \times 10^{-3}$ | 4.34 |
| 140-17 (Cl, 5-OMe) | $1.9 \times 10^{-3}$ | 1.1 |
| 140-62 (H, 6-OMe) | $3.8 \times 10^{-5}$ | 6.49 |
| 140-73 (Cl, 6-OMe) | $5.5 \times 10^{-5}$ | 2.22 |
| AMPPD | $6.4 \times 10^{-4}$ | 8.2 |
| CSPD | $6 \times 10^{-3}$ | 4.5 |

To demonstrate positively the interaction of the dioxetane, or at least the excited-state emitter, with enhancement agents of the type known for use in connection with dioxetanes, the wavelength for the emission maximum was detected in the absence of any enhancement agent, in the presence of BDMQ, and on a nylon membrane. The data are set forth in the following table.

| | Emission Max, nm | | |
|---|---|---|---|
| Dioxetane | No Addition | +BDMQ | On Nylon |
| 128-70 | 471 | 463 | 461 |
| 128-87 | 470 | 464 | 459 |
| 140-20 | 476 | 466 | 461 |
| 140-17 | 475 | 464 | 463 |
| 140-62 | 490 | 482 | 477 |
| 140-73 | 487 | 479 | 481 |

DOT BLOT ASSAYS

As noted above, the dioxetanes of this invention are suitable for use in dot blot assays. The dioxetanes synthesized according to the synthesis route described above were employed in dot blot assays. In confirmation of the absence of chemiluminescence of the dioxetanes bearing a Z substituent at the six position, it should be noted that Compound 140-62 gave a consistent absence of signal, or, under optimum conditions, a barely detectable signal.

Similarly, the dioxetane with the methoxy substituent at the six position with a chlorine substituent on the adamantyl ring, 140-73, gave no signal in dot blot assay, again confirming the lack of chemiluminescent activity in six-substituted metaphosphate phenyl dioxetanes.

Nitrocellulose and nylon membranes were spotted with a biotinylated 35 base oligonucleotide probe. The probe was diluted in 1× SSC to yield a starting dilution of 210 pg.

Successive 1:2 dilutions of the starting dilution were spotted on the membranes, 12 spots total. The membranes were dried, subjected to optimum UV crosslinking (120 mJ/cm²), blocked for 30 minutes in blocking buffer (nitrocellulose: 0.2% I-Block, 0.1% Tween-20, 1× PBS; nylon: 0.2% I-Block, 0.5% SDS, 1× PBS), incubated 20 minutes in a 115000 dilution of streptavidin-alkaline phosphatase conjugate diluted in blocking buffer, and washed as follows: 1×5 minutes in blocking buffer; 3×5 minutes in 1×PBS, 0.3% Tween-20 (nitrocellulose) or 3×5 minutes in 1× PBS, 0.5% SDS (nylon); 2×5 minutes in substrate buffer (0.1 M diethanolamine, 0.1 mM $MgCl_2$, pH 10); 1×5 minutes in a 1/20 dilution of Nitro-Block (Tropix, Inc., Bedford, Mass.) diluted in substrate buffer (Nitrocellulose Experiment Only); and 2×5 minutes in substrate buffer (Nitrocellulose Experiment Only). The membranes were incubated with 0.25 mM dioxetane diluted in substrate buffer for 5 minutes. Several membranes in both the nitrocellulose and nylon experiments were incubated with 0.25 mg/ml Calfax DB-45, Calfax 10L-45 or Calsoft T-60 (Pilot Chemical Company, Los Angeles, Calif.), 1.0 mg/ml Tween-20, 1.0 mg/ml Nitro-Block, and 0.25 mM dioxetane diluted in substrate buffer for 5 minutes. These membranes were not subjected to a 1/20 dilution of Nitro-Block. The membranes were then exposed to x-ray film and developed.

Thus, as can be seen from the results above, electron withdrawing groups added to the aromatic ring of the dioxetane slow the kinetics of light emissions while tending to increase the chemiluminescent signal. In contrast, electron-donating groups accelerate $T_{1/2}$, apparently by facilitating electron transfer from the oxygen, through the aromatic group, to the dioxetane. Thus, by proper selection of the nature and ability of the electron-donating or electron-withdrawing Z substituent, and simultaneous selection of the appropriate substituent for the adamantyl ring, if desired, dioxetanes of specific characteristics, including optimized signal intensity, optimized speed, specific emission wavelength, and the like, can be obtained.

These dioxetanes can be used for assays of all types in which an enzyme capable of cleaving the dioxetane can be attached to one element of the ultimate complex which the analyte, if present, will form. Conventional assay formats are known to those of skill in the art, and are described in the patents set forth above in the Background of the Invention. Exemplary disclosure of suitable assays appears in U.S. Pat. No. 5,112,960, and the same is incorporated herein by reference. The assay format, per se, save for the enhanced performance therein by the dioxetanes of this invention, does not constitute an aspect of the invention.

The dioxetanes of this invention, as well as the intermediates therefore, have been disclosed by reference to both generic description and specific embodiment. Additionally, dioxetane performance has been described generally, and exemplified. The examples are not intended as limiting, and should not be construed as such. Variations in substituent pattern, identity, and the like, consistent with the disclosure will occur to those of ordinary skill in the art. Such variations and modifications remain within the scope of the invention, save as excluded by the positive limitations set forth in the claims below.

What is claimed is:

1. A method of detecting the presence of a target substance in a sample, wherein said target substance is a ligand which is bound by a second member of a ligand binding pair, comprising:

combining said sample with a complex of said second member of said ligand binding pair and an enzyme, under conditions which permit binding of said ligand binding pair if said target is present in said sample, removing from said sample all said complex which is not bound, adding a dioxetane of the formula I:

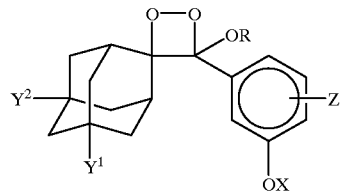

(I)

wherein $Y^1$ and $Y^2$ are independently H, a hydroxyl group, a halogen, an unsubstituted lower alkyl group, a hydroxy lower alkyl group, a halo lower alkyl group, a phenyl group, a halo phenyl group, an alkoxy phenyl group, an alkoxy phenoxy group, a hydroxy alkoxy group, a cyano group, an amide group, an alkoxy group or a carboxyl group, wherein R is C1–12 alkyl, aryl or aralkyl, wherein X is an enzyme-labile group selected from the group consisting of a phosphate, galactoside, acetate, 1-phospho-2,3-diacylglyceride, 1-thio-D-glucoside, adenosine triphosphate, adenosine diphosphate, adenosine monophosphate, adenosine, α-D-glucoside, β-D-glucoside, β-D-glucuronide, α-D-mannoside, β-D-mannoside, β-D-fructofuranoside, β-glucosiduronate, P-toluenesulfonyl-L-arginine ester, and P-toluenesulfonyl-L-arginine amide, and wherein Z is an electron-active group selected from the group consisting of electron withdrawing groups and electrondonating groups and occupies the four or five position on the phenyl ring, to said sample, and monitoring said sample for chemiluminescence emission, wherein said enzyme cleaves said enzyme-labile group and said emission is indicative of the presence of said target compound in said sample.

2. The method of claim 1, wherein said chemiluminescence emission is quantified, and wherein the amount of chemiluminescence emission is directly related to the amount of said target in said sample.

* * * * *